(12) United States Patent
Yoshida et al.

(10) Patent No.: US 11,717,245 B2
(45) Date of Patent: Aug. 8, 2023

(54) X-RAY FLUOROSCOPIC IMAGING APPARATUS

(71) Applicant: SHIMADZU CORPORATION, Kyoto (JP)

(72) Inventors: Koki Yoshida, Kyoto (JP); Fumiaki Tanaka, Kyoto (JP); Ryusuke Watanabe, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 139 days.

(21) Appl. No.: 17/535,015

(22) Filed: Nov. 24, 2021

(65) Prior Publication Data
US 2022/0249048 A1 Aug. 11, 2022

(51) Int. Cl.
*A61B 6/00* (2006.01)

(52) U.S. Cl.
CPC ............ *A61B 6/485* (2013.01); *A61B 6/4441* (2013.01); *A61B 6/461* (2013.01)

(58) Field of Classification Search
CPC ....... A61B 6/485; A61B 6/4476; A61B 6/461; A61B 6/4441; A61B 6/54; A61B 6/44; A61B 6/56; A61B 6/107; A61B 6/40; A61B 6/4452; A61B 6/467; A61B 6/548; A61B 6/12; A61B 6/4447; A61B 6/487; A61B 6/4085; A61B 6/542; A61B 6/587; A61B 6/04; A61B 6/547; A61B 6/0487; A61B 6/0407; A61B 6/588; A61B 6/102; A61B 6/42; A61B 6/505; A61B 6/50; A61B 6/4208; A61B 6/504; A61B 6/466; A61B 6/022; H02G 11/00; H04N 13/00; H04N 13/361; H04N 13/117; H04N 13/128; H04N 2013/0081; G06T 15/00
USPC .......................................................... 378/44
See application file for complete search history.

(56) References Cited

U.S. PATENT DOCUMENTS

| | | | |
|---|---|---|---|
| 6,334,708 B1 | 1/2002 | Kosugi | |
| 2005/0151498 A1* | 7/2005 | Bauer | A61B 6/4441 318/575 |
| 2008/0175354 A1* | 7/2008 | Wang | A61B 6/4441 378/197 |

(Continued)

FOREIGN PATENT DOCUMENTS

| | | | | |
|---|---|---|---|---|
| EP | 3552549 A1 * | 10/2019 | ........... | A61B 6/4441 |
| JP | 2000-197621 A | 7/2020 | | |

*Primary Examiner* — Irakli Kiknadze
(74) *Attorney, Agent, or Firm* — Andrew F. Young, Esq.; Nolte Lackenbach Siegel

(57) ABSTRACT

An X-ray fluoroscopic imaging apparatus executes an operation of rotating a C-arm continuously using a sequence mode function. The apparatus including a C-arm 9 that supports an X-ray tube 5 and an X-ray detector 7 facing each other, a memory storage element 37 stores a plurality of positions information relative to the C-arm 9 corresponding to an order information related to rotation of C-arm 9 to such a position as a sequence information, a touch panel 43 displays the position information included in the sequence information in parallel along the order of rotation of the C-arm 9, and a display control element 55 controls the touch panel 43 to display the next target rotation information, at which the C-arm 9 irradiates the X-ray, among the position information included is a sequence information SQ1 in a predetermined fixed region R1 of the touch panel 43.

5 Claims, 16 Drawing Sheets

(56) References Cited

U.S. PATENT DOCUMENTS

| | | | | |
|---|---|---|---|---|
| 2018/0325610 A1* | 11/2018 | Cameron | ............. | A61B 5/1072 |
| 2018/0333132 A1* | 11/2018 | Noda | .................... | A61B 6/581 |
| 2018/0368792 A1* | 12/2018 | Yoshida | ............... | A61B 6/4208 |
| 2021/0138271 A1* | 5/2021 | Hugger | ................ | A61N 5/1065 |

* cited by examiner

| Rotation order (Order information J) | Registered C-arm rotation position | Rotation direction and Rotation Angle | | | |
|---|---|---|---|---|---|
| | | Body axis direction | | Body axis circumference | |
| | | CRA | CAU | LAO | RAO |
| J1 → 01 | Rotation position F1 | 30° | – | 30° | – |
| 02 | Rotation position F2 | 40° | – | 20° | – |
| 03 | Rotation position F3 | 0° | 0° | 0° | 0° |
| 04 | Rotation position F4 | 30° | – | – | 30° |
| 05 | Rotation position F5 | 25° | – | – | 10° |
| 06 | Rotation position F6 | – | 30° | – | 30° |
| 07 | Rotation position F7 | – | 60° | – | 40° |
| 08 | Rotation position F8 | – | 30° | 30° | – |
| J9 → 09 | Rotation position F9 | – | 20° | 45° | – |

X-RAY FLUOROSCOPIC IMAGING APPARATUS

CROSS REFERENCE TO RELATED APPLICATIONS

This application relates to, and claims priority from, JP 2021-018945 filed Feb. 9, 2021, the entire contents of which are incorporated herein by reference in complete detail.

FIGURE SELECTED FOR PUBLICATION

FIG. 12

BACKGROUND OF THE INVENTION

Field of the Invention

The present invention relates to an X-ray fluoroscopic imaging apparatus that performs an X-ray fluoroscopy or an X-ray imaging in multiple directions by rotating the apparatus in the body axis direction and around the body axis of a subject while the X-ray tube and the X-ray detector are facing each other.

Description of the Related Art

When an operative procedure using an examination and an operation using a catheter procedure in the circulatory field, e.g., a cardiovascular disorder, is performed in the medical field, the X-ray fluoroscopic imaging apparatus that performs an X-ray fluoroscopy or an X-ray imaging is now mandatory. In such an operative procedure, the fluorescence imaging is performed by irradiating the circulatory region of the subject with the X-ray in an arbitrary direction. The operator performs the examination or the operative procedure while referring to the X-ray image data acquired by the fluoroscopic imaging.

The X-ray fluoroscopic imaging apparatus has an imaging system consisting of a table on which the subject is loaded, an X-ray tube and an X-ray detector and a C-shape arm (C-arm) supporting the imaging system. The X-ray tube and the X-ray detector are installed to one end and the other end respectively of the C-arm and the C-arm is set to allow the X-ray tube and the X-ray detector to face each other while sandwiching the subject. The C-arm is rotatable in the body axis direction and the circumference direction of the body axis of the subject (here in after "rotation direction") with a predetermined rotation angle. The C-arm rotates to an arbitrary rotation position (in the arbitrary rotation direction and with the arbitrary angle), so that the X-ray can be irradiated from an arbitrary direction to the subject to acquire the X-ray image.

When the examination or the operational procedure is performed for circulatory organs, the target region is imaged from a plurality of directions and then a diagnosis is performed, so that an operation to rotate the C-arm in series to a plurality of the rotation positions is needed. Given all operations are conducted manually, the workload on the operator increases, so that it is proposed that recently, the X-ray fluoroscopic imaging apparatus having a sequence mode function (order operation mode function) that sets up in advance the position to which the C-arm rotates and the order of rotation to such a position is proposed (e.g., refer to Patent Document 1).

When the sequence mode is executed, the operator registers the information of a plurality of rotation positions in advance before performing the examination and sets up the information of the order in which the rotation (shift) takes place to such a rotation position. According to such a setting procedure, the sequence information, in which the information of a plurality of rotation positions and the information of the order in which the rotation (shift) takes place to such a rotation position are associated respectively, is stored in a memory.

And the sequence information is read out from the memory at an examination step and the list of the sequence information is displayed on a monitor. The operator instructs the C-arm to start an action to perform the rotation in accordance with the sequence information referring the sequence information displayed on the monitor. The C-arm rotates in series to the plurality of rotation positions being set up in the sequence information following such an instruction followed by irradiating the X-ray from the X-ray tube toward the subject at the respective rotation positions.

Specifically, the C-arm rotates to the rotation position (target rotation position) at which the C-arm rotates for irradiating the X-ray following the irradiation of the X-ray to the predetermined rotation position. And, once the C-arm shifts to the target rotation position, the X-ray is irradiated from the X-ray tube due to the instruction of the operator. In such a way, while the C-arm is rotating automatically to a plurality of target rotation positions, the X-ray image can be acquired at each target rotation position based on the sequence mode function in which the rotation to the target rotation position according to the predetermined rotation order and then the X-ray irradiation at such a target rotation position take place repeatedly.

RELATED PRIOR ART

Patent Document 1-JP 2000-197621 A1

ASPECTS AND SUMMARY OF THE INVENTION

Objects to be Solved

Nevertheless, in the case of a conventional example having such structure, following problems are remained to be solved.

Conventionally, terms denoting the rotation position information of the C-arm are in a rotation order with regard to the sequence information displayed on the monitor while executing sequence mode functions. Specifically, the respective rotation position information included in the sequence information are listed on the display. In such a case, the operator must identify the rotation position information corresponding to the target rotation position at the present time from all listed rotation positions. Accordingly, the operator must cast an eye at all rotation position information displayed on the monitor, so that it can be difficult to understand the target rotation position of the X-arm at the present time.

A configuration that may facilitate to understand the target rotation position information of the C-arm at the present time may be the configuration in which only the target rotation position information at the present time among all rotation position information is displayed in an emphasis manner different from other terms. For example, only a region which displays the target rotation position information at the present time may be displayed in a different color from others. However, in such a configuration, the operator has to find out the rotation position information displayed in the different manner from all rotation position information while moving the own sight all over the monitor. Accordingly, even if it is structurally displayed in the different manner, it is hard to solve the problem in which fatigue due to understanding the target rotation position information at the present time is accumulated.

Considering such circumstances, the purpose of the present invention is to provide an X-ray fluoroscopic imaging apparatus capable of executing further easily the operation to rotate the C-arm continuously using the sequence mode function.

Means for Solving the Problem

The present invention constitutes the following structure to achieve such a purpose.

Specifically, the X-ray fluoroscopic imaging apparatus of the present invention comprises: an X-ray tube that irradiates an X-ray to a subject; an X-ray detector that is in place to face the X-ray tube and detects the X-ray transmitting the subject; a support mechanism that supports the X-ray tube and the X-ray detector while facing each other and rotatable around the respective two axes that are orthogonal to each other; a rotation position detection element that detects the information related to the position of the support mechanism as a position information; a memory storage element that stores a plurality of position information so as to correspond to the order information for the support mechanism that rotates to such a position, as the sequence information; a position information display element that displays the position information included in the sequence information in parallel and in order of the rotation of the support mechanism; a display control element that controls the position information display element to display the position information corresponding to the target position, which is the position of the support mechanism that irradiates next the X-ray, among the position information included in the sequence information, in the predetermined fixed region of the position information display element every time when the X-ray tube irradiates the X-ray.

According to such a configuration, the memory storage element stores the position information related to the position of the support mechanism in connection with the order information to rotate to such a position as the sequence information. The position information display element displays the respective position information included in the sequence information in parallel and in the rotation order of the rotation mechanism. When the position information display element displays the respective position information, the display control element controls the position information display element to display the position information corresponding to the target position that is the position of the support mechanism, which irradiates next the X-ray, in the predetermined fixed region of the position information display element.

Next, the position information corresponding to the target position that is the position of the support mechanism that performs next to irradiate the X-ray is constantly in the fixed region, so that the operator can absolutely understand the position information of the target position at the present time by casting the eye at such a fixed region of the position information display element. Accordingly, even when a number of the position information included in the sequence information are displayed in parallel on the position information display element, the operator can find out easily and quickly the position information of the target position from such a number of the position information. In addition, even when the target position of the support mechanism is changed in series due to proceeding the sequence mode, the operator can confirm the information of the target position of the support mechanism without moving the sight from the fixed region. Accordingly, the fatigue of the operator due to moving the eyesight constantly while executing the sequence mode function can be prevented.

According to the present invention set forth above, it is preferable that the fixed region is the center region of the position information display element.

Action and Effect

According to the X-ray fluoroscopic imaging apparatus of the present invention, the operator casts an eye at the center region of the position information display element, so that the information of the target position of the support mechanism can be absolutely confirmed. The center region of the position information display element is the region that is the relatively easy region to be visually recognized, so that the operator can further easily understand the information of the target position of the support mechanism by fixing the region to be in the center region, in which the information of the target position of the support mechanism is displayed.

According to the present invention set forth above, it is preferable that the display control element controls the position information display element to display the position information corresponding to the position, to which the support mechanism rotates next and at which the X-ray is irradiated following the target position at the present time, adjacent to the position information corresponding to the target position displayed in the fixed region.

[Action and Effect] According to the X-ray fluoroscopic imaging apparatus of the present invention, not only the position information corresponding to the target position of the support mechanism at the present time is displayed in the fixed region of the position information display element, but also the position information corresponding to the next position to which the support mechanism rotates can be displayed adjacently. In such a case, the operator can understand the position information of the position at which the X-ray is irradiated following the next rotation of the support mechanism, i.e., the next target position, in addition to the target position of the support mechanism at the present time, with moving slightly the sight from the fixed region. Therefore, the operator can understand quickly the information of the position that is the next target position and proceeds appropriately the examination or the operation procedure while predicting the trajectory of the support mechanism that rotates from the next target position at the present time to the position of the target position and the rotation timing of the support mechanism.

According to the present invention set forth above, it is preferable that the display control element controls the position information display element to display the position information corresponding to the position at which the X-ray is irradiated following the latest rotation of the support mechanism, the position information corresponding to the target position of the support mechanism at the present time, and the position information corresponding to the position at which the X-ray is irradiated following the next rotation of the support mechanism to the target position at the present time are adjacently displayed respectively in series.

[Action and Effect] According to the X-ray fluoroscopic imaging apparatus of the present invention, the position information corresponding to the position at which the X-ray is irradiated following the latest rotation of the support mechanism, the position information corresponding to the target position displayed in the fixed region and the information of the position at which the X-ray is irradiated following the next rotation of the support mechanism at the present time are displayed adjacently and respectively in series.

The information of the position at which the X-ray is irradiated following the latest rotation of the support mechanism, i.e., the information of the position which is the latest target position is the highly important information as well as the information of the target position at the present time and the information of the position to be next target position while executing the sequence mode. And the information of such three positions are adjacently displayed to one another, so that the operator can understand three position information with moving slightly the sight from the fixed region. Specifically, the operator understands the rotation trajectory of the support mechanism right before and right after with no fatigue. Accordingly, the operator can predict more precisely the respective rotation trajectory and the rotation timing of the support mechanism, so that the examination and the procedural operation can be proceeded more adequately.

According to the present invention set forth above, it is preferable that a position information selection element that selects the predetermined number of the position information including the position information corresponding to the target position of the support mechanism at the present time among a plurality of the position information included in the sequence information is included and the display control element displays the predetermined number of the position information selected by the position information selection element on the position information display element.

Action and Effect

According to the X-ray fluoroscopic imaging apparatus of the present invention, the position information selection element and the display control element selectively display the predetermined number of the position information including the position information corresponding to the target position of the support mechanism at the present time among the plurality of the positions. Specifically, even when the sequence information includes a number of position information, the number of the position information to be displayed on the position information display element can be limited to the predetermined number. Accordingly, a visibility (visual recognition level) of the position information displayed on the position information display element, particularly, the visibility of the information relative to the target position of the support mechanism at the present time can be improved.

Effects of the Present Invention

According to the X-ray fluoroscopic imaging apparatus of the present invention, the memory storage element stores the position information related to the position of the support mechanism in connection with the order information to rotate to such a position as the sequence information. The position information display element displays the respective position information included in the sequence information in parallel along the order of rotation of the rotation mechanism. When the position information display element displays the respective position information, the display control element controls the position information display element to display the position information corresponding to the target position that is the position of the support mechanism, which irradiates next the X-ray, in the predetermined fixed region of the position information display element.

Next, the position information corresponding to the target position that is the position of the support mechanism that performs irradiation of the X-ray is constantly displayed in the fixed region, so that the operator can absolutely understand the position information of the support mechanism at the present time by casting the eye at such a fixed region of the position information display element. Accordingly, even when a number of the position information included in the sequence information are displayed in parallel on the position information display element, the operator can find out easily and quickly the position information of the support mechanism at the present time from such a number of the position information.

In addition, even when the target position of the support mechanism is changed in series due to proceeding the sequence mode, the operator can confirm the information of the present position of the support mechanism, which is changed in series, without moving the sight from the fixed region. Accordingly, an accumulation of the fatigue of the operator due to moving the sight constantly while executing the sequence mode function can be prevented, the operation to rotate continuously the support mechanism using the sequence mode can be further easily executed.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 4 is a list table illustrating the rotation positions included in the sequence information

DETAILED DESCRIPTION OF THE PREFERRED EMBODIMENTS

Figure 1:
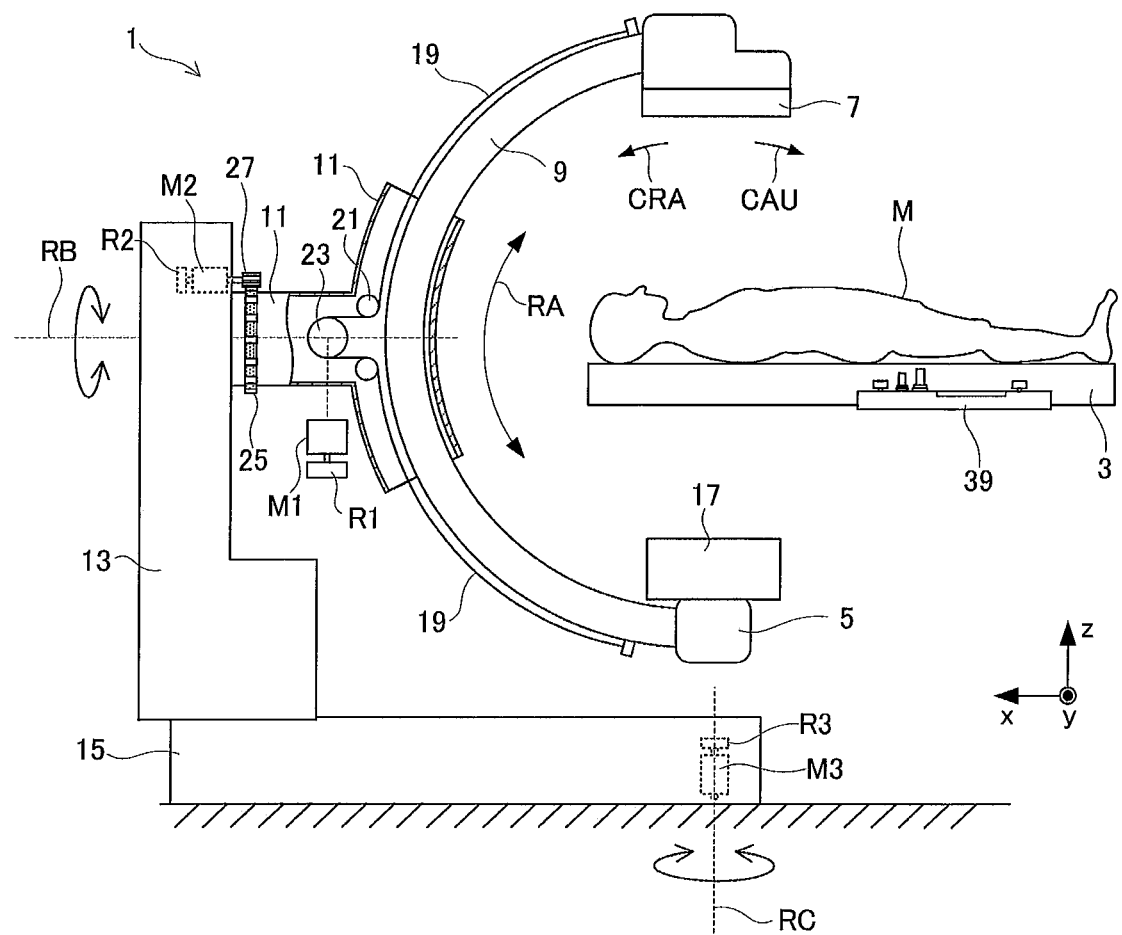
FIG. 1 is a front view illustrating the entire structure of an X-ray the fluoroscopic imaging apparatus according to the Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Referring to Figures, the inventor sets forth the Embodiment of the present invention.

(Illustration of the Entire Structure)

Figure 2:
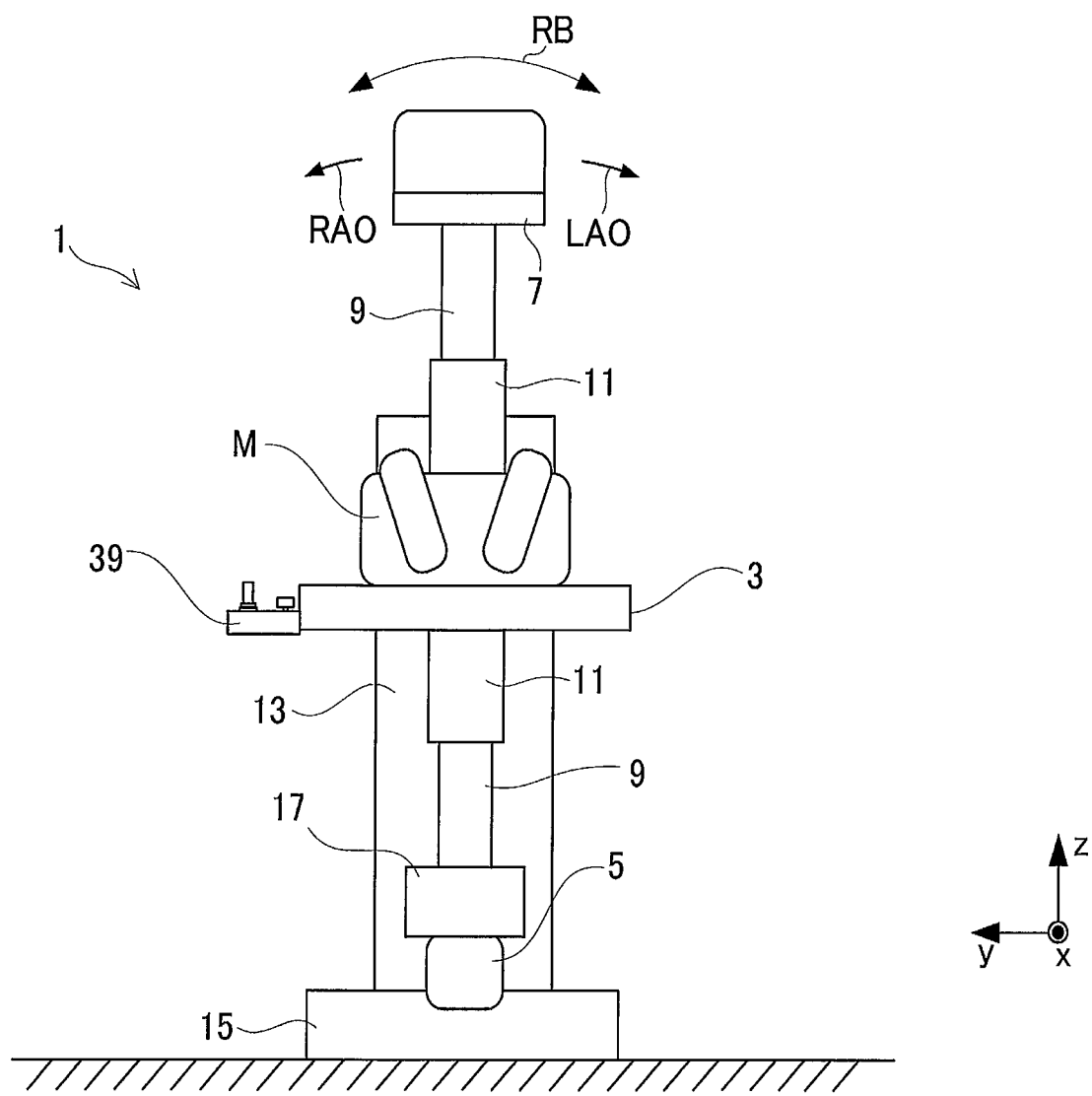
FIG. 2 is a right-side view illustrating the entire structure of the X-ray fluoroscopic imaging apparatus according to the Embodiment.

Referring to FIG. 1 and FIG. 2, an X-ray fluoroscopic imaging apparatus 1 according to the Embodiment comprises an X-ray tube 5 and an X-ray detector 7 which are facing each other while sandwiching the subject M on the table 3 in a supine posture. The X-ray tube 5 irradiates the X-rays to the subject M. The X-ray detector 7 detects the X-ray, which is irradiated from the X-ray tube 5 to the subject M and transmits therethrough and converts to an electric signal and then outputs the electric signal as an X-ray detection signal. One example of the X-ray detector 7 is such as a flat panel detector (FPD).

The X-ray tube 5 the X-ray detector 7 are respectively installed to a C-arm 9. The C-arm 9 has an approximately C-like bending shape. The X-ray tube 5 is installed to one end of the C-arm 9 and the X-ray detector 7 is installed to the other end of the C-arm 9. The C-arm 9 that is held by the arm holding member 11 capable of sliding along the circular arc pathway of the C-arm 9 indicated by the sign RA. The C-arm 9 rotates around the axis orthogonal to the body axis (hereinafter body axis direction) of the subject M.

The arm holding member 11 that is installed to the side portion of the supporting column 13 is configured to rotate around the horizontal axis RB parallel to the x-direction (long side direction of the table 3 and also called around the body axis) and body axis direction). The C-arm 9, which is held by the arm holding member 11, rotates around the body axis of the subject M in accordance with rotation of the arm holding member 11.

According to the present Embodiment as set forth above, the C-arm 9 rotates independently around two axes orthogonal to each other (e.g., the body axis direction of the subject M and the circumference direction of the body axis). In addition, the direction consisting of the body axis direction of the subject M and the circumference direction of the body axis thereof the subject M is called (collectively) hereinafter "rotation direction". The C-arm 9 rotates freely and respectively around the orthogonal two axes to each other along the respective arch path RA and arch path RB, so that X-rays can be irradiated to the subject M from arbitrary directions. The C-arm 9 corresponds to the support mechanism of the present invention.

In addition, referring to FIG. 1 and FIG. 2, the state in which the X-ray tube 5 and the X-ray detector 7 are perpendicular relative to the subject M is the initial (default) state of the X-arm. And the rotation position of the C-arm 9 in the initial state is defined as the default position of the C-arm 9. With regard to the default position of the C-arm 9, the rotation angle of the C-arm is specified as 0° for the respective body axis direction and circumference direction of body axis.

The support column 13 that is supported by the support pedestal base 15 installed to the floor surface is movable horizontally in the y-direction (short side direction of the table 3). The arm holding member 11 and the C-arm 9 supported by the support column 13 move in the y-direction following the horizontal move of the support column 13. The collimator 17 installed below the X-ray tube 5 limits X-rays irradiated from the X-ray tube 5 to a predetermined shape. An example of the predetermined shape may be a cone shape similar to a pyramid.

Next, the inventors set forth the rotation mechanism of the C-arm 9. The rotation of the C-arm 9 in the body axis direction of the subject M is achieved using a driving mechanism inside the arm holding member 11. A part of a belt 19 of which both ends are fixed to the C-arm 9 is housed inside the arm holding member 11, and the belt 19 is bridged with a driving roller 23 through a guide roller 21.

A driving motor M1 and a rotary encoder R1 are attached inside the arm holding member 11. The driving motor M1 rotates the driving roller 23. The rotary encoder R1 detects the rotation direction and rotation of the driving motor M1. The C-arm 9 rotates in the body axis direction of the subject M through the belt 19 due to the rotation of the rotation motor 11. In addition, for convenience of explanation, referring to FIG. 1, the driving motor M1 and the rotary encoder R1 are shown outside the arm holding member 11.

The rotation of the C-arm 9 in the circumference direction of the body axis of the subject M is achieved by rotating the arm holding member 11 in the circumference direction of the horizontal axis RB, i.e., the circumference direction of the body axis of the subject M. The pedestal portion of the arm holding member 11, i.e., the opposite end of the side holding the C-arm 9, is supported with the side portion of the support column 13 so as to be rotatable and a gear 25 is fixed near the support plane.

The gear 25 is occluded with a pinion gear and the pinion gear 27 is mounted on the output shaft of the driving motor M2 installed inside the support column 13. The C-arm 9 rotates in the circumference direction of the body axis of the subject M together with the arms holding member 11 due to rotation of the driving motor M2. The rotary encoder R2 detects the rotation direction and rotation of the driving motor M2.

The driving motor M3 and the rotary encoder R3 are attached inside the support pedestal base 15. The driving motor M3 rotates the support pedestal base 15 in the circumference direction of the perpendicular axis RC by rotating the driving mechanism, not shown in FIG. For example, the perpendicular axis RC is an axis extending axis in the perpendicular direction through the X-ray tube and the X-ray detector 7 at the default position referring to FIG. 1. The rotary encoder R3 detects the rotation direction and rotation of the driving motor M3. The support pedestal base 15 rotates, so that the arm holding member 11 with the support pedestal base 15 and the C-arm 9 swirl and move in the circumference direction of the perpendicular axis RC.

Figure 3:
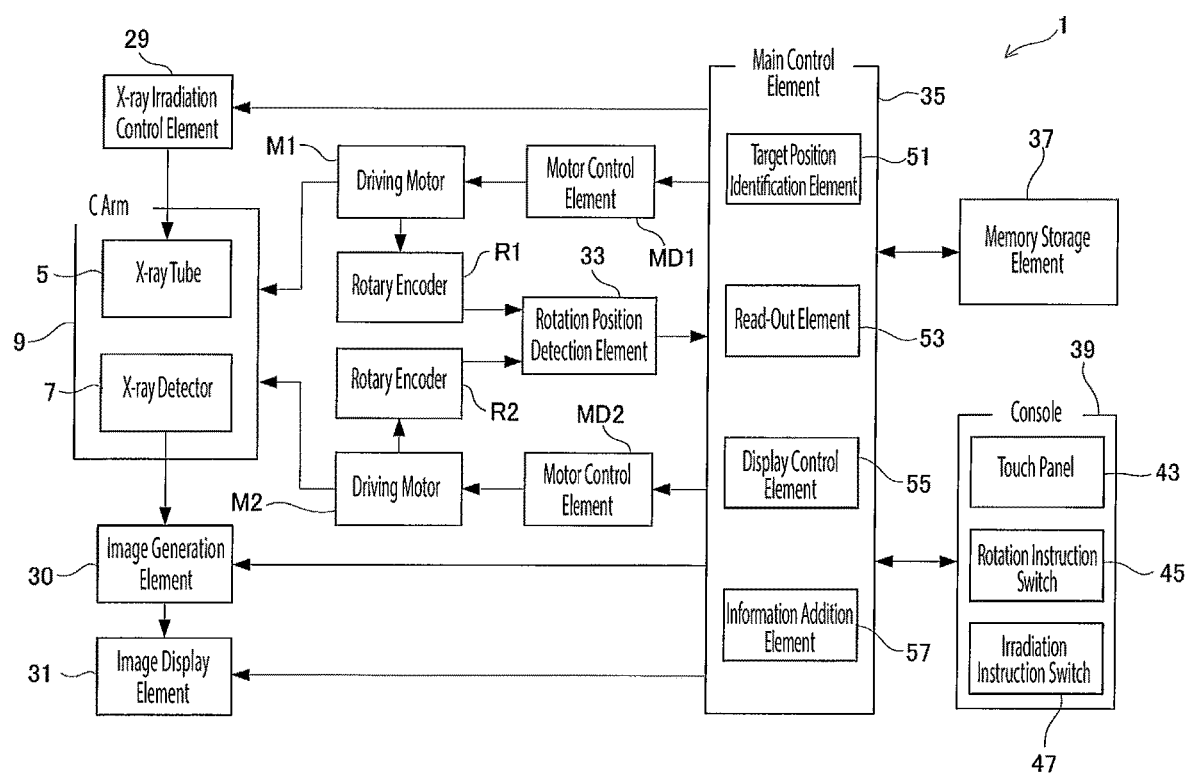
FIG. 3 is a schematic functional block diagram illustrating the X-ray fluoroscopic imaging apparatus according to the Embodiment.

Referring to FIG. 3, the X-ray fluoroscopic imaging apparatus 1 further comprises an X-ray irradiation control element 29, an image generation element 30, an image display element 31, a motor control element MD1, a motor control element MD2, a rotation position detection element 33, a main control element 35, a memory storage element 37 and a console 39. The X-ray irradiation control element 29 is configured to output a high voltage to the X-ray tube 5. And the amount of X-ray irradiated by the X-ray tube 5 and the timing of X-ray irradiation are controlled based on the high voltage output provided by the X-ray irradiation control element 29.

The image generation element 30 that is installed to the latter part of the X-ray detector 7 generates an X-ray image based on the X-ray detection signal output from the X-ray detector 7. The image display element 31 that is installed to the latter part of the image generation element 30 displays the X-ray images generated by the image generation element 30. An example of the image display element 31 is a liquid crystal monitor. As a structural example, the image display element 31 is hanging from ceiling or loaded on a movable wheeled platform.

The motor control element MD1 is installed in the upstream of the driving motor M1 and controls the rotation direction and rotation of the driving motor M1. The motor control element MD2 is installed in the upstream of the driving motor M2 and controls the rotation direction and rotation of the driving motor M2. The X-ray fluoroscopy imaging apparatus 1 further comprises the motor control element MD3, not shown in FIG., and the motor control element MD3 controls of the rotation direction and rotation of the driving motor M3.

The rotation position detection element 33 detects the rotation position of the C-arm 9 based on the rotation direction and rotation of the driving motor M1 detected by the rotary encoder R1 and the rotation direction and rotation of the driving motor M2 detected by the rotary encoder R2. The rotation position of the C-arm 9 is identified according to the rotation direction and rotation of the C-arm 9.

The rotation direction of the C-arm 9 is expressed as follows. Referring to FIG. 1, with regard to the body axis direction of the subject M, the head side direction thereof is denoted in CRA (cranial) hereinafter and the foot side direction thereof is denoted in CAU (caudal) hereinafter. And referring to FIG. 2, with regard to the circumference direction of the body axis of the subject M, the rotation direction to the left side from the head side direction thereof is denoted in LAO (left anterior oblique) hereinafter and the rotation direction to the right side from the head side thereof is denoted in RAO (right anterior oblique) hereinafter.

The rotation direction of the C-arm 9 is specified by a combination of the rotation direction (CRA or CAU) of the C-arm 9 in the body axis directions of the subject M and the rotation direction (LAO or RAO) of the C-arm 9 in which the C-arm 9 in the circumference direction of the subject M. And the rotation angle of the C-arm 9 is specified by a combination of the rotation angle of the C-arm 9 in the body axis directions of the subject M and the rotation angle of the C-arm 9 in the circumference direction of the body axis of the subject M.

A rotation position detection element 33 calculates the rotation direction and rotation angle of the C-arm 9 which rotates in the body axis direction of the subject M based on the information of the rotation direction and rotation of the driving motor M1, which the rotary encoder R1 sends. And the rotation position detection element 33 detects the rotation direction and rotation angle of the C-arm 9 which rotates in the circumference direction of the body axis of the subject M based on the information of the rotation direction and rotation of the driving motor M2, which the rotary encoder R2 sends. And then, the rotation direction and rotation angle of the C-arm 9 is calculated based on such information.

A main control element 35 comprises an information processing means, such as a central processing unit (CPU) as an example. The main control element 35 controls comprehensively a variety of components of the X-ray fluoroscopic imaging apparatus 1, e.g., the motor control element MD1, the motor control element MD2, the X-ray irradiation control element 29, the image generation element 30 and the image display element 31.

The memory storage element 37 stores a variety of information, e.g., the information as to the X-ray imaging condition including such as the tube voltage and the tube electric current, a variety of X-ray images generated by the image generation element 30 and the information related to the image processing with the image generation element 30. An example of the memory storage element 37 is a non-volatile memory. In addition, the memory storage element 37 stores the information related to the rotation position of the C-arm 9 and also is configured to store the sequence information.

The sequence information includes the information related to the rotation position of the C-arm 9 and each of a plurality of the rotation position information corresponds to the order information of the rotation of the C-arm 9. In addition, the sequence information that the memory storage element 37 can store is not limited to one and the memory storage element 37 may store individually a plurality of sequence information.

In the present Embodiment, it is deemed that the memory storage element 37 has stored the sequence information SQ1 referring to FIG. 1 in advance. The sequence information SQ1 includes the information of nine rotation positions F1-F9. The rotation position F1-F9 are lined up according to the rotation order of the C-arm 9 in the sequence information SQL Specifically, the rotation position F1 is set up to be the first position at which the C-arm 9 rotates to irradiate an X-ray at the beginning and the rotation position F2 is set up to be the second position at which the C-arm 9 rotates to irradiate an X-ray at the second time. The rotation position F9 is set up to be the last position at which the C-arm 9 rotates to irradiate an X-ray at the end.

Referring to FIG. 4, the rotation position F1 is the position following rotation 30° from the default position in the LAO direction and also 30° in the CRA direction. The rotation position F2 is the position following rotation 20° from the default position in the LAO direction and also 40° in the CRA direction. The rotation position F3-F9 are as is denoted in FIG. 4, so that the explanations are skipped.

A console 39 is used to input the operator's instruction relative to the operation of the X-ray fluoroscopic imaging apparatus 1, and the main control element 35 conducts a comprehensive control following the instruction which the operator inputs using the console. Examples of the console 39 includes e.g., a key-board panel, a touch input panel, a mouse, a dial, and a change switch, and a push button switch.

According to the present Embodiment, referring to FIG. 1, the console 39 is attached to the side portion of the table 3. In such a case, the operator stands near by the table 3 and operates the console 39 while standing. The console 39 is attached to the table 3, so that the operator can a variety of operations as for the X-ray fluoroscopic imaging apparatus 1 while performing a catheter procedure or an examination for the subject M.

In addition, the console 39 is not limited to be attached to the side portion of the table 3, and the top plane of the removable wheeled platform may be equipped with the console 39. In addition, the console 39 is not limited to be in place in the long side portion of the table 3, and the console 39 may be attached to the short side portion of the table 3.

Figure 5:
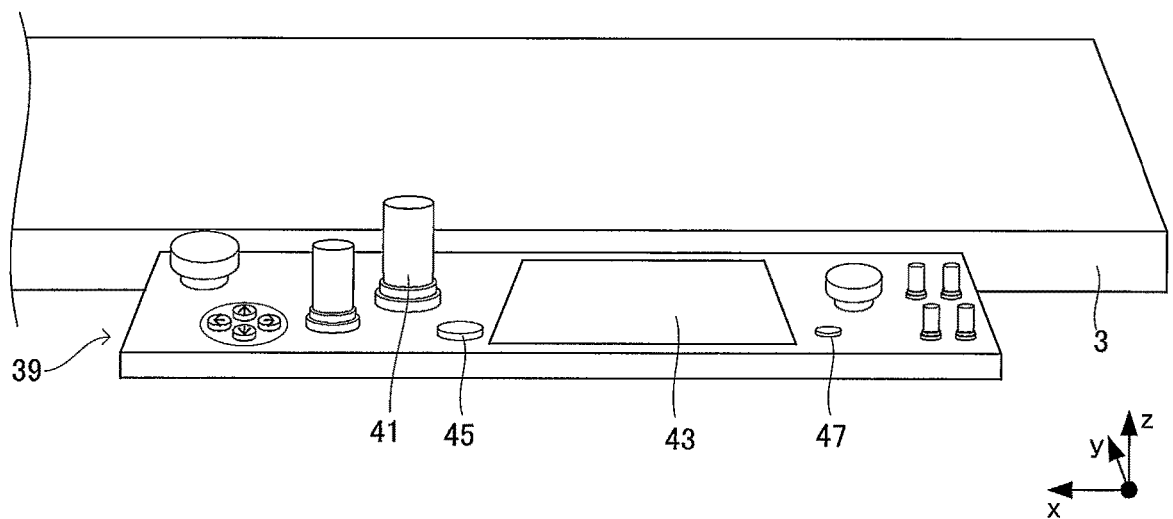
FIG. 5 is a perspective view illustrating an input element according to the Embodiment.

Next, the inventors set fort essential operation devices installed to the console 39. Referring to FIG. 5, the console 39 comprises the arm operation lever 41, the touch panel 43, the rotation instruction switch 45 and the imaging instruction switch 47.

The arm operation lever 41 is configured to be tiltable back and forth and around and adjusts the rotation position of the C-arm 9. For example, provided the operator grips the arm operation lever 41 and tilts forth, the C-arm 9 rotates in the LAO direction. The rotation angle of the C-arm 9 changes corresponding to the tilt angle of the arm operation lever 41 or the time period of tilting. Further, provided the operator grips the arm operation lever 41 and tilts to the left direction, so that the C-arm 9 rotates in the CRA direction. The operator can manually and finely adjust the rotation position of the C-arm using the arm operation lever 41.

The touch panel 43 runs a variety of operations such as an operation for storing the rotation position of the C-arm 9 and an operation for storing the sequence information to continuously rotate the C-arm 9 and displays many iconic switches. In addition, when executing a rotation operation of the C-arm 9 due to the sequence mode, the touch panel 43 display the ongoing executing sequence information. The inventors set forth the structure of the touch panel 43 that displays the sequence information. The touch panel 43 corresponds to the position information display element of the present invention.

A rotation instruction switch 45 is a push button switch for moving the C-arm 9 to the predetermined rotation position. Specifically, provided the rotation instruction switch 45 is pushed down under the state in which the specific rotation position is selected, the C-arm 9 rotates toward such a specific rotation position.

The imaging instruction switch 47 is a push button switch and operated to input an instruction for generating an X-ray image. The X-ray is irradiated from the X-ray tube 5 to the subject M when the operator pushes down the imaging instruction switch 47. The X-ray irradiated from the X-ray tube 5 is detected by the X-ray detector 7, and the image generation element 30 performs a variety of calculation processings (image processings) to generate the X-ray image based on the signal detected by the X-ray detector 7.

In addition, the inventors set forth while limiting the four operation devices related to adjustment of the rotation position of the C-arm 9, but the device installed to the console 39 is not limited to such four devices. Specifically, an operation device as to the operation of the X-ray fluoroscopic imaging apparatus 1 such as a switch to turn on and off of the main electric power, a switch to set up the imaging conditions, a switch to adjust the position of the table 3, or an emergency shutdown switch to stop can be arbitrary installed.

Referring to FIG. 3, the main control element 35 further comprises a target position identification element 51, a read-out element 53, a display control element 55 and an information addition (providing) element 57. The target position identification element 51 identifies the target rotation position of the C-arm 9 at the present time corresponding to the proceeding status of the rotation operation of the C-arm 9 due to the sequence mode.

The target rotation position is the rotation position as a destination of the rotation of the C-arm 9, at which the X-ray tube 5 irradiates the X-ray followingly. For example, the target rotation position is the rotation position F1 at the time when the sequence mode initiates based on the sequence information SQ1. And the C-arm 9 rotates to the rotation position F1 and once the X-ray is irradiated at the rotation position F1, the target rotation position is changed from the rotation position F1 to the rotation position F2. In such a way, every time the X-ray is irradiated from the X-ray tube 5 to the subject M, the information of the target rotation position that is identified by the target position identification element 51 is changed.

The read-out element 53 selects and reads out the preset predetermined number of rotation position information from a plurality of rotation position information included in the sequence information that is stored in the memory storage element 37. According to the present Embodiment, it is set up so that up to four kinds of rotation position information are read out by the read-out element 53 including the information of the target rotation position at the present time. The content of the rotation position information read out by the read-out element 53 is arbitrary changed corresponding to the proceeding status of the sequence mode. The read-out element 53 corresponds to the position selection element of the present invention.

The display control element 55 controls the touch panel 43 to display the information of the rotation position that the read-out element 53 reads out. In addition, the display control element 55 controls the display format of the touch panel 43 to display the information of the target rotation position of the C-arm 9 at the present time constantly on the predetermined prefixed region of the touch panel 43 from the read-out rotation position information. According to the present Embodiment, the touch panel 43 is controlled to display the information of the target rotation position of the C-arm 9 at the present time constantly in the first region R1.

The information addition element 57 displays the additional information as to the read-out rotation position information that the read-out element 53 reads out on the touch panel 43. Examples of the additional information may include the information implying the target rotation position at the present time from the read-out rotation position information at the present time (target display information) and the information implying that the C-arm 9 reaches to the target rotation position (reaching completion information), but not limited thereto.

<Structure of the Touch Panel>

Figure 6:
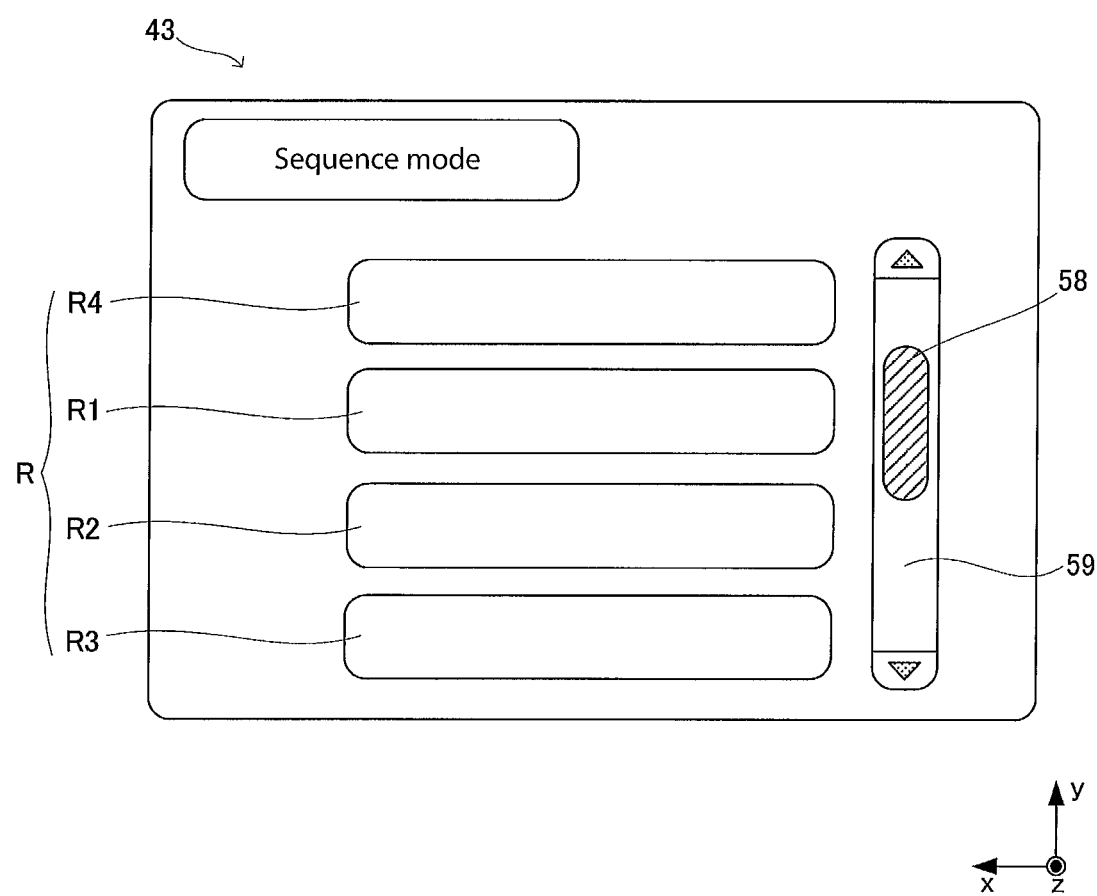
FIG. 6 is a view illustrating a display screen in the sequence mode of the touch panel according to the Embodiment.

Next, the inventors set forth the structure of the touch panel 43 in detail. FIG. 6 is a view illustrating a display screen of the touch panel 43 while executing the sequence mode.

The touch panel 43 further comprises a display region R. The display region R is the region at which the information of the rotation position, and the display region R includes the display regions R1-R4 that are four regions according to the present Embodiment, The display regions R1-R4 are the fixed regions at which the read-out information read out by the read-out element 53 are displayed and in place in series of the display region R4, R1, R2 and R3 from top to bottom of the touch panel 43. According to the present Embodiment, the display region R1 is in place in the screen center region of the touch panel 43. Accordingly, the display region R2 is on the lower side of the display region R1 and near by the display region R1. The display region R3 is in the lower side of the display region R2 and near by the display region R2. And the display region R4 is in the upper side of the display region R1 and near by the display region R1.

The information of the rotation position corresponding to the target rotation position at the present time from the rotation position information read out by the read-out element 53 is constantly displayed in the display region R1. Therefore, while executing the sequence mode, the operator casts an eye at the display region R1 that is in place in the screen center region of the touch panel 43 and can understand absolutely the information of the target rotation position at the present time.

The information of the rotation position of the next target rotation position from the target rotation position at the present time is displayed in the display region R2. The information of the rotation position of the next target rotation position of the rotation position displayed in the display region R2 is displayed in the display region R3. Therefore, the operator visually recognizes such as the display region R2 with casting slightly the eye at the lower side of the touch panel 43 from the display region R1 and accordingly, can understand the pathway of the C-arm 9 following the target rotation position at the present time.

The information of the rotation position that is the target rotation position right before the target rotation position at the present time is displayed in the display region R4. For example, provided the target rotation position at the present time is the rotation position F6, the information of the rotation position F7 is displayed in the display region R2, the information of the rotation position F8 is displayed in the display region R3 and the information of the rotation position F5 is displayed in the display region R4. The operator visually recognizes such as the display region R4 with casting slightly the eye at the upper side of the touch panel 43 from the display region R1 and accordingly, can understand the pathway of the C-arm 9 from the latest target rotation position to the target rotation position at the present time.

The touch panel 43 further comprises a seekbar 58 and a scroll bar 59. The seekbar 58 indicates the relative order of the rotation positions displayed in the display region R1-R4 from the total rotation positions of the sequence information SQ1. For example, the operator can understand an approximate order of the rotation positions displayed in the display region R1-R4 from the total rotation positions of the sequence information SQ1 by visually recognizing the position of the seekbar 58 relative to the scroll bar 59.

The scroll bar 59 is configured to change manually the information of the rotation position displayed in the display region R1-R4. Specifically, the information of the rotation position displayed in the display region R1 can be temporally changed from the information of the target rotation position at the present time to the information of the rotation position before or after such a target rotation position by operating the scroll bar 59. In addition, the information of the rotation position displayed in the display region R1 can be returned to the information of the target rotation position at the present time by pressing down the reset button, not shown in FIG.

<Overview of the Operation Using the Sequence Mode>

Figure 7:
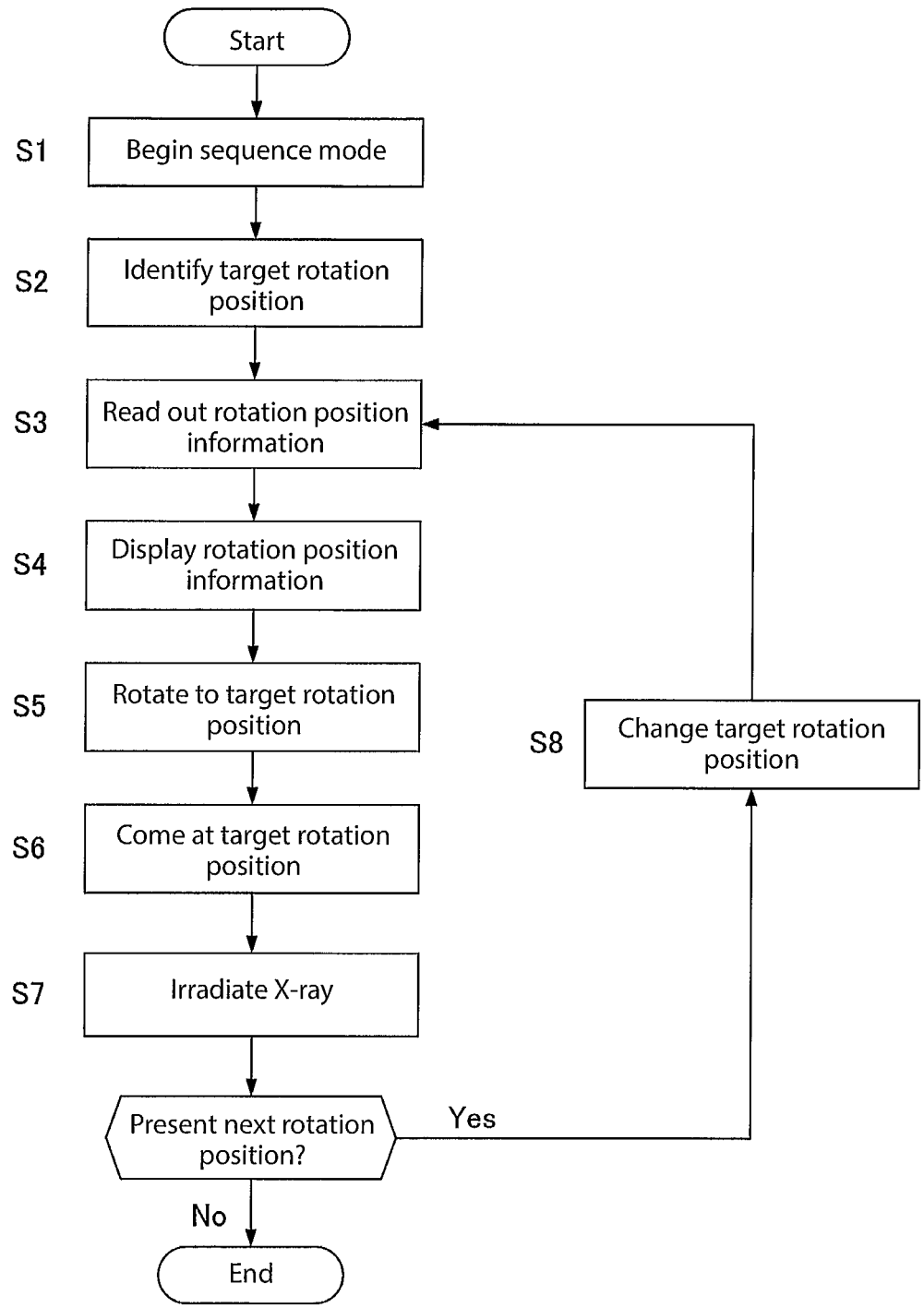
FIG. 7 is a flow chart illustrating steps of the sequence mode of the X-ray fluoroscopic imaging apparatus according to the Embodiment.

Next, the inventors set forth the overview of the operation using the sequence mode with regard to the X-ray fluoroscopic imaging apparatus 1 according to the present invention. Referring to FIG. 7, the flow chart to acquire the X-ray images from a plurality of positions by rotating continuously the C-arm 9 due to the sequence mode.

Step S1 (Initiate the Sequence Mode)

First, the operator starts the touch panel 43 of the console 39 and operates the start button, not shown in FIG., arranged in such as the touch panel 43 to input the instruction for starting the sequence mode (Step S1). According to the present Embodiment, the operator selects the sequence information SQ1 from a plurality of the sequence information stored in the memory storage element 37 and then, inputs the instruction to start the sequence mode using the sequence information SQ1.

Step S2 (Identification of the Target Rotation Position)

Once the instruction to start the sequence mode is input, the action to identify the target rotation position at the present time is executed by the target position identification element 51. The target position identification element 51 identifies the rotation position at which the X-ray is irradiated next as the target rotation position. In addition, according to the present Embodiment, the rotation position at which the X-ray is irradiated next means the rotation position of the C-arm 9 at the timing when the X-ray is irradiated in the nearest future from the present time as the basis therefor. In other words, the target rotation position is the position as the destination for rotation of the C-arm 9 at which the next X-ray irradiation is performed at the present time as the basis therefor.

Figure 8:
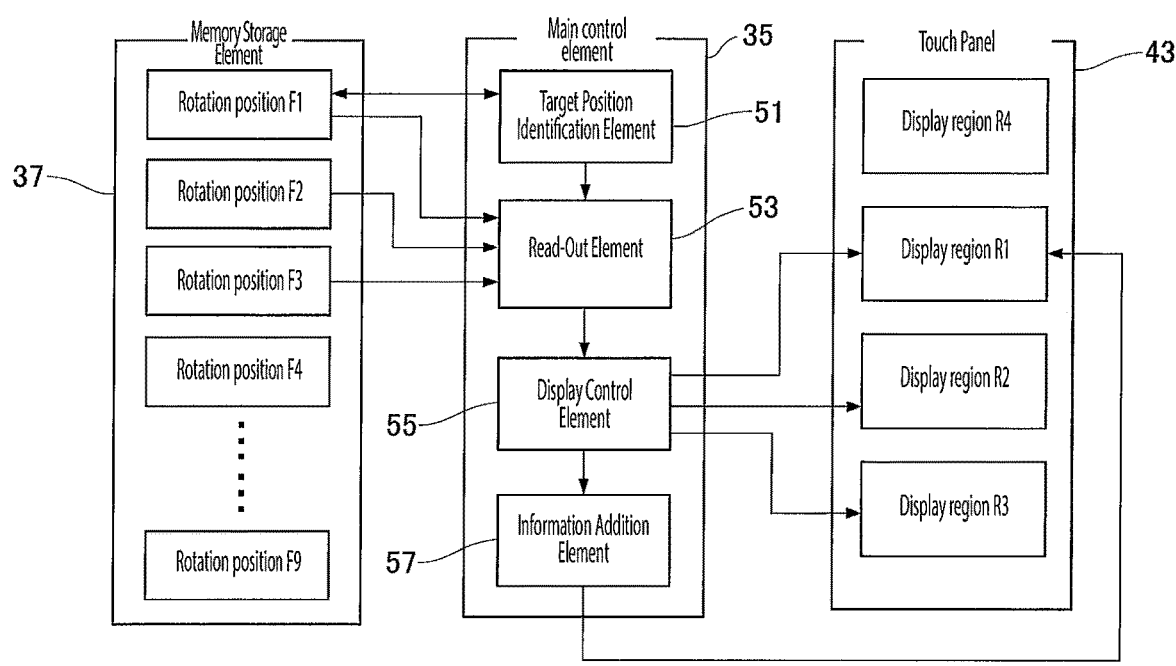
FIG. 8 is a functional block diagram illustrating the essential elements of the X-ray fluoroscopic imaging apparatus, when the target rotation position at the present time is the rotation position F1 according to the Embodiment.

The rotation position as the destination of rotation of the C-arm 9 to irradiate the X-ray next is the rotation position F1 at the start point of the sequence mode. Accordingly, referring to FIG. 8, the target position identification element 51 identifies the rotation position F1 as the target rotation position at the present time from the rotation positions F1-F9 included in the sequence information SQL Specifically, the target rotation position corresponds to the target position of the present invention.

Step S3 (Read Out the Rotation Position Information)

Once the target rotation position is identified, the information of the predetermined number of the rotation positions from a plurality of the rotation position information included in the sequence information SQ1 is read out from the memory storage element 37. Specifically, the read-out element 53 identifies the information of the rotation position that is the object read out from the memory storage element 37 corresponding to the information of the target rotation position at the first stage of Step S3. And the read-out element 53 reads out the information of the rotation position identified as the read-out object from the memory storage element 37 at the second stage of Step S3.

The rotation position information as the read-out object is identified based on the information of the rotation position that is the object to be displayed in the display region R of the touch panel 43. The rotation position F1 that is the first rotation position of the C-arm 9 is the target rotation position at the start point of the sequence mode. In addition, when the target rotation position is the rotation position F1, the rotation positions that are the objects to be displayed in the display regions R1-R3 as set forth later are the rotation positions F1-F3 and on the other hand, the information of the rotation position to be the object being displayed in the display region R4 does not exist.

Accordingly, provided the rotation position F1 that is the first rotation position of the C-arm 9 is the target rotation position at the present time, the rotation positions to be the object being displayed on the touch panel 43 are the rotation position F1, rotation position F2 and the rotation position F3. Accordingly, referring to FIG. 8, the read-out element 53 identifies the rotation position F1, the rotation position F2 and the rotation position F3 from the sequence information SQ1 as the rotation position information that is the object to be displayed on the touch panel 43. And the read-out element 53 reads out the information of the rotation position F1, the rotation position F2 and the rotation position F3 from the memory storage element 37.

Step S4 (Display the Rotation Position Information)

The display control element 55 determines the region at which the respective read-out rotation positions information are displayed based on the relationship with the target rotation position. First, the rotation position F1 is identified as the target rotation position from the rotation positions F1-F3. And the display object of the display region R1 is the target rotation position at the present time. Therefore, the target rotation position of display control element 55 controls the touch panel 43 to display the information of the rotation position F1 in the display region R1.

Next, the rotation position that is the target rotation position next to the target rotation position at the present time is the display object in the display region R2. The rotation position of the C-arm 9 next to the rotation position F1 is the rotation position F2 relative to the sequence information SQ1. In other words, the target rotation position next to the rotation position F1 is the rotation position F2. Therefore, provided the target rotation position at the present time is the rotation position F1, the rotation position F2 is the display object in the display region R2. Consequently, the display control element 55 controls the touch panel 43 to display the information of the rotation position F2 in the display region R2.

And the display object of the display region R3 is the rotation position to be the target rotation position next to the display object in the display region R2. The rotation position to be the target rotation position next to the rotation position F2 is the rotation position F3. Consequently, provided the target rotation position at the present time is the rotation position F1, the rotation position F3 is the display object in the display region R3. Then, the display control element 55 controls the touch panel 43 to display the information of the rotation position F3 in the display region R3.

Figure 9:
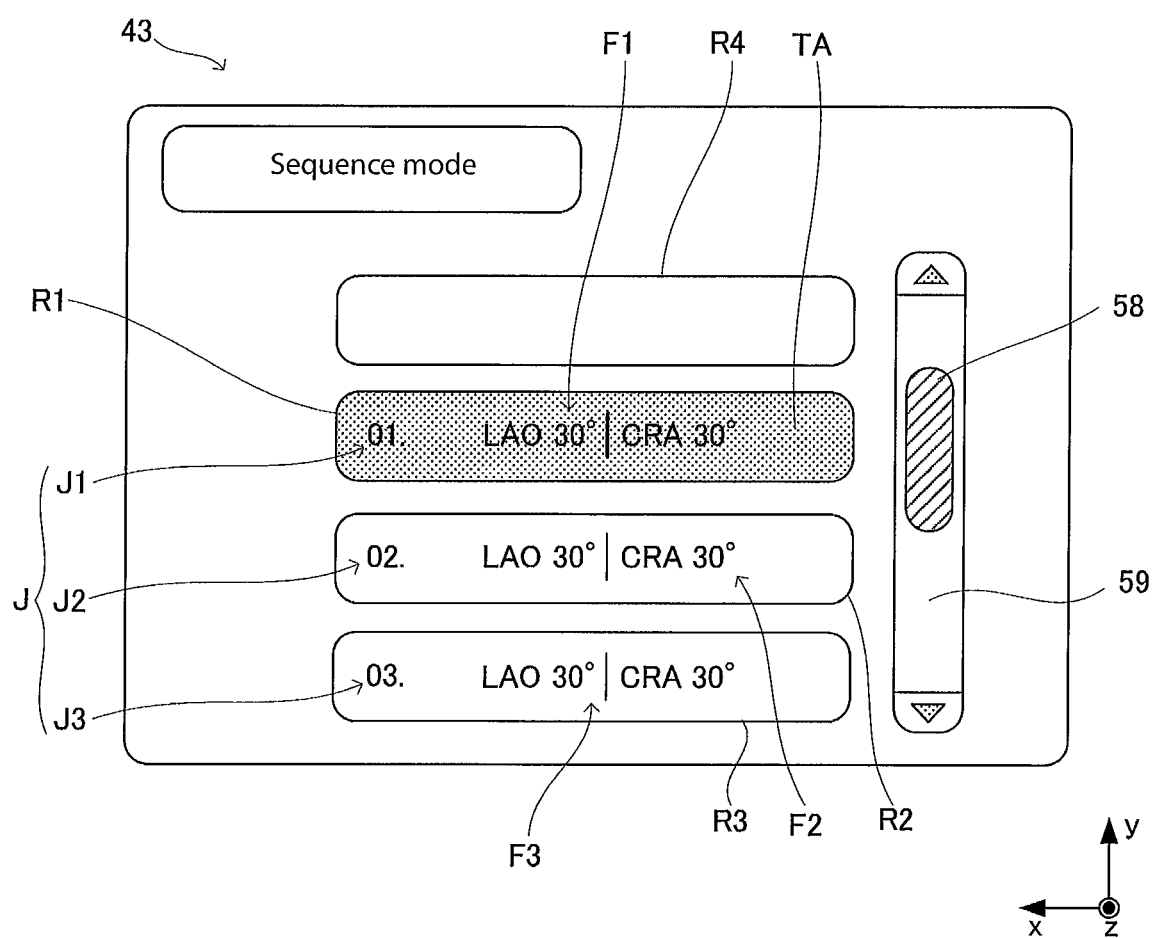
FIG. 9 is the view illustrating the touch panel display screen at the Step S4 when the target rotation position at the present time is the rotation position F1 according to the Embodiment.

The display object in the display region R4 is the information of the latest target rotation position. Provided the target rotation position is the rotation position F1, no latest target rotation position exists, so that no display object exists in the display region R4. Then, the display control element 55 controls the touch panel 43 to display none in the display region R4. As a result, provided the target rotation position identified in Step S2 is the rotation position F1, the display screen of the touch panel 43 is as is illustrated in FIG. 9.

The order information in which the C-arm 9 rotates to such a rotation position is displayed in the respective display regions R1-R4 in correspondence with the information of the respective rotation positions. Specifically, the order information J1 indicating that the rotation order of the C-arm 9 is first is corresponding to the position information of the rotation position F1. And the rotation position F1 and the order information J1 are displayed in the display region R1. The order information J2 indicating that the rotation order of the C-arm 9 is second is corresponding to the position information of the rotation position F2 and displayed in the display region R2. The order information J3 indicating that the rotation order of the C-arm 9 is third is corresponding to the position information of the rotation position F3 and displayed therein.

The display control element 55 controls the touch panel 43, and the information addition element 57 also adds the additional information TA to the display region R2 in which the target rotation position is displayed. The additional information TA is the information indicating that the position information displayed in the display region R2 among the rotation positions displayed on the touch panel 43 is the target rotation position and also that the C-arm 9 has not yet reached to such a target rotation position. According to the present Embodiment, the additional information TA displays the entire display region R2 in a different color from other display regions R1, R3 and R4. Referring to FIG. 9, the entire area of the display region R2 indicates the additional information TA using a halftone pattern.

The operator can confirm the information of the target rotation position at the present time by visually recognizing the rotation position F1, the order information J1 and the additional information TA while casting an eye at region R2 corresponding to the center region of the touch panel 43. Specifically, it can be understood by visually recognizing such information displayed in the display region R2 that the target rotation position at the present time is the rotation position F1 that is the position to which the C-arm 9 rotates first, and the information indicates that the C-arm 9 has not rotated to such a rotation position F1.

Step S5 (Rotates to the Target Rotation Location)

The operator executes the operation for rotating the C-arm 9 to the target rotation position following confirming the target rotation position at the present time. Specifically, once the operator pushes down the rotation instruction switch 45, the C-arm 9 starts rotation toward the rotation position F1 from the default position. According to the present Embodiment, the rotation action of the C-arm 9 is executed while the operator is pushing down the rotation instruction switch 45. In addition, the rotation action of the C-arm 9 is suspended once the operator unlinks a hand from the rotation instruction switch 45.

Step S6 (Reach to the Target Rotation Position)

The C-arm 9 reaches to the rotation position F1 from the initial position when the operator continuously pushes down the rotation instruction switch 45. Once the C-arm 9 reaches to the rotation position F1, i.e., the target rotation position, the information of arrival at the rotation position F1 is sent from the rotation position detection element 33 to the main control element 35. Once the information with regard to the arrival of the C-arm 9 at the target rotation position is received, the information addition element 57 changes the information to be added to the display region R2 from the additional information TA to the additional information TB referring to FIG. 10.

Figure 10:
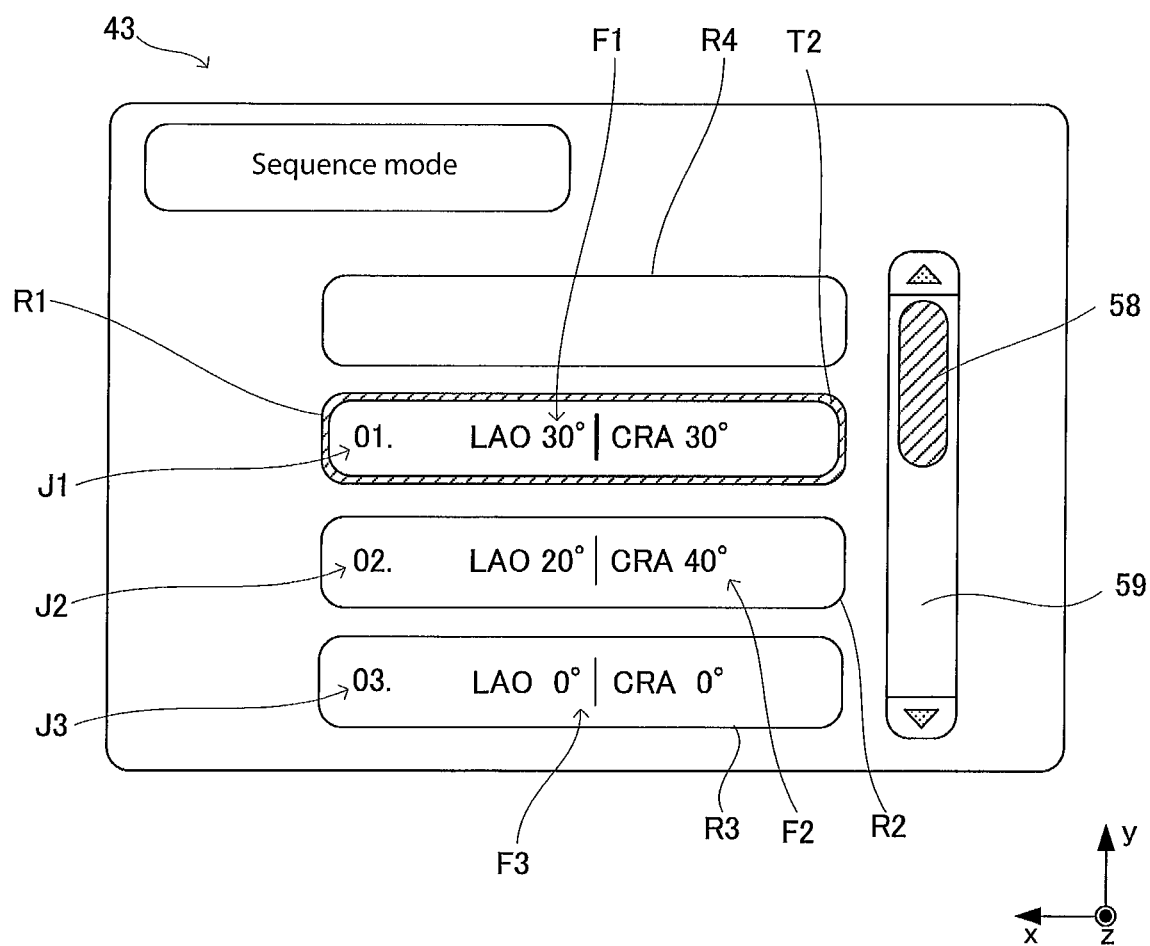
FIG. 10 is the view illustrating the touch panel display screen at the Step S5 when the target rotation position at the present time is the rotation position F1 according to the Embodiment.

The additional information TB is the information indicating that the position information displayed in the display region R2 among the rotation positions displayed in the touch panel 43 is the target rotation position and also the proceeding in which the C-arm 9 has reached to such a target rotation position. According to the present Embodiment, the additional information TB is the information for displaying the outer circumference region of the display region R2 in a different color from other display regions R1, R3 and R4. Referring to FIG. 10, the outer circumference region of the display region R2 indicates the additional information TB using slant lines. The operator can confirm that the X-ray can be irradiated since the C-arm 9 arrives at the target rotation position by visually recognizing that the information added to the display region R2 is changed from the additional information TA to the additional information TB.

Step S7 (Irradiate the X-Ray)

The operator executes the operation to irradiate the X-ray to the subject M and acquire the X-ray image following confirming the target rotation position at the present time. Specifically, the instruction is input to irradiate the X-ray by pressing down the imaging instruction switch 47 attached to the console 39. The X-ray is irradiated from the X-ray tube 5 installed to the C-arm 9 to the subject M due to the operation of the imaging instruction switch 47. The X-ray detector 7 detects the X-ray and outputs the X-ray detection signal, and the image generation element 30 executes a variety of image processings based on such detected signals and generates the X-ray image.

The following step branches depending on existence or nonexistence of the rotation position to which the C-arm 9 rotates next following the X-ray irradiation. If the rotation position to which the C-arm 9 rotates next exists, the step proceeds to Step S8. If the target rotation position is the rotation position F1, the C-arm 9 must rotate to the rotation position F2 next, so that the action relative to Step S8 is executed.

Step S8 (Change the Target Rotation Position)

Figure 11:
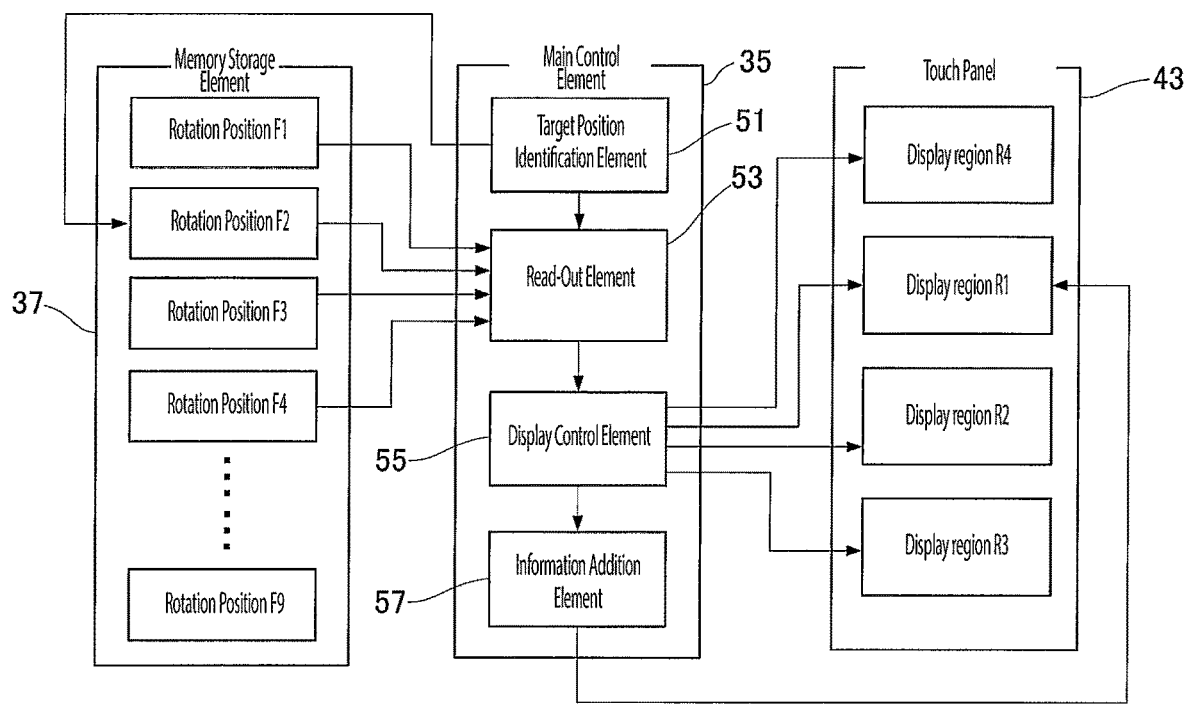
FIG. 11 is a functional block diagram illustrating the essential elements of the X-ray fluoroscopic imaging apparatus, when the target rotation position at the present time is the rotation position F2 according to the Embodiment.

If the rotation position to which the C-arm 9 rotates next, i.e., if the next target rotation position exists, the action to change the target rotation position is executed following the X-ray is irradiated. Specifically, the target position identification element 51 changes the information of the rotation position that identifies the target rotation position as the trigger that is the action to irradiate the X-ray from the X-ray tube 5. Once the X-ray irradiation at the rotation position F1 is completed, the rotation position at which the X-ray is irradiated next is the rotation position F2. Accordingly, referring to FIG. 11, the target position identification element 51 changes the rotation position, which is identified as the target rotation position, from the rotation position F1 to the rotation position F2 in association with the X-ray irradiation action at the rotation position F1 as a trigger. In such a way, with regard to the X-ray fluoroscopic imaging apparatus 1 according to the present Embodiment, once the X-ray irradiation is completed, the target rotation position is automatically changed.

Once Step S8 is completed and the target rotation position is changed, the action returns to Step S3 and then after, the above action is repeated. Specifically, either action of Step S3 or Step S7 is executed under the state in which the target rotation position at the present time is the rotation position F2. Provided the target rotation position at the present time is the rotation position F2, the latest target rotation position is the rotation position F1. Therefore, the object displayed in the display region R4 is the rotation position F1. In addition, the object displayed in the display region R2 is the rotation position F3, and the object displayed in the display region R3 is the rotation position F4.

Accordingly, the target rotation position at the present time is changed to the rotation position F2, so that the information of the four rotation positions F1-F4 is read out from the memory storage element 37 by the read-out element 53 in Step S3. Consequently, referring to FIG. 12, in Step S4, the touch panel 43 is controlled by the display control element 55 so that the information of the rotation position F2 together with the order information J2 is displayed in the display region R1.

And the information of the rotation position F3 together with the order information J3 is displayed in the display region R2, and the information of the rotation position F4 together with the order information J4 is displayed in the display region R3. And the information of the rotation position F1 together with the order information J1 is displayed in the display region R4. In Step S4, the C-arm 9 has not reached to the target rotation position at the present time, so that the information addition element 57 displays additionally the additional information TA in the display region R1.

The operator visually recognizes the display region R1 and the display region R4 in place near by the upper side of the display region R1, so that the operator can easily and quickly understand the pathway on which the C-arm 9 rotates when the rotation instruction switch 45 is operated in Step S5. Specifically, the specific information of the rotation position F1 is displayed in the display region R4, and the specific information of the rotation position F2 is displayed in the display region R1 to which the additional information TA is added.

Therefore, the operator can understand in advance that the C-arm 9 rotates from the rotation position F1 to the rotation position F2 when the rotation instruction switch 45 is pushed down at the present time. Accordingly, provided an obstacle is in the pathway from the rotation position F1 to the rotation position F2, the operator can intuitively understand an incident being interfered with the obstacle while the C-arm 9 is rotating before executing the process of Step S5. Therefore, the rotation action of the C-arm 9 in Step S5 can be adequately executed by operating the rotation instruction switch 45 following a removal of the obstacle in advance.

In addition, the display region R1 and the display region R2 which is near by lower side of the display region R1 are visually recognized, so that the operator can understand the pathway on which the C-arm 9 rotates from the target rotation position at the present time to the next target rotation position and the time needed for the rotation thereof. Specifically, the rotation position F2 and the rotation position F3 are visually recognized, so that the future position of the C-arm 9 and the timing thereof can be predicted. Therefore, the operator considers the speed of the own skills and the rotation position of the C-arm 9 from now and can understand the necessary procedure to perform adequately the operation and the extermination in advance.

The display region R1 is the fixed region at the center of the touch panel 43 and the display region R2 is the region near by the display region R1. Therefore, the operator can absolutely understand the information of the target rotation position at the present time and the information of the next target rotation position with taking a simple action to cast the eye at the center of the touch panel 43, Accordingly, it is not necessary for the operator to find out the target information by casing the eye at the entire area of the touch panel 43 when confirming the important information to proceed adequately the sequence mode. As a result, the workload for the operator to confirm the information can be reduced and the time needed to confirm the information thereof can be shortened.

Figure 12:
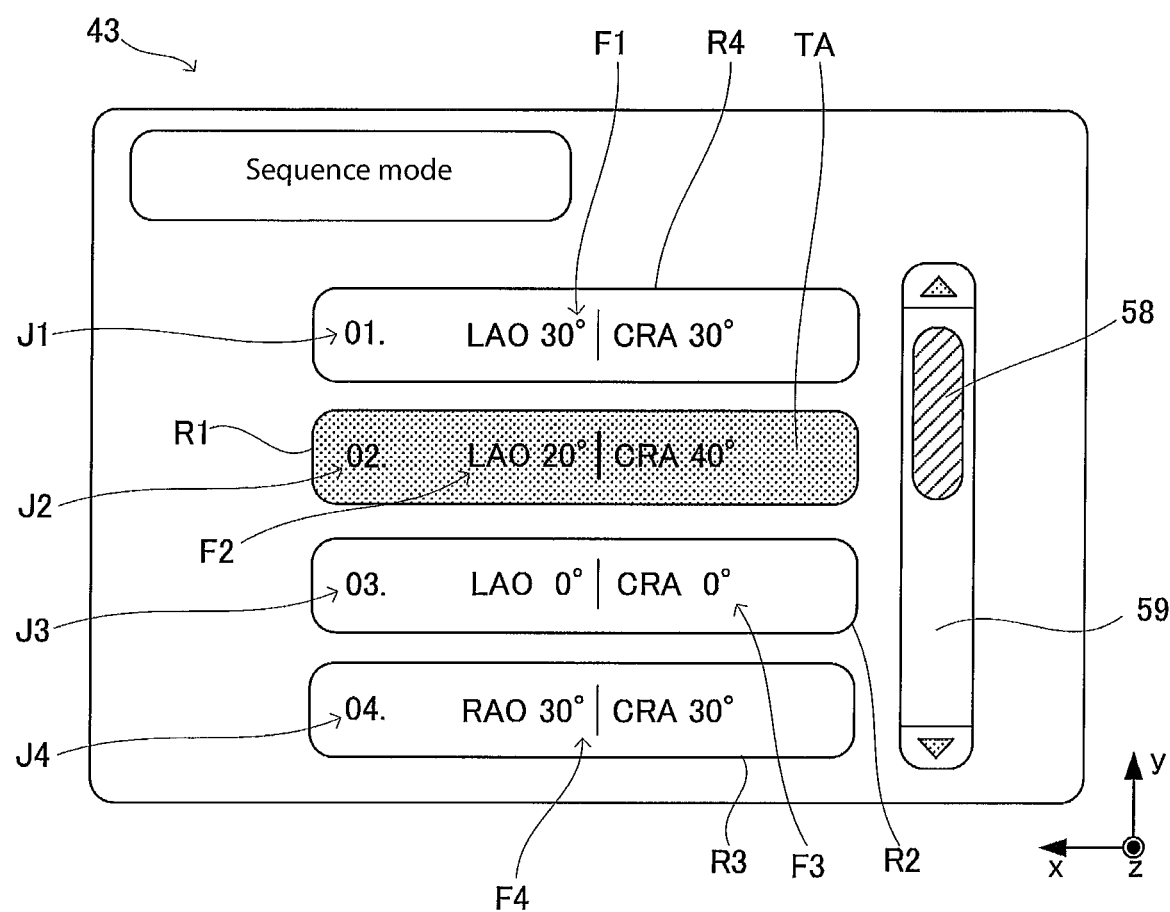
FIG. 12 is the view illustrating the touch panel display screen at the Step S4 when the target rotation position at the present time is the rotation position F2 according to the Embodiment.

The operator executes the following step while understanding the information of the rotation positions F1 and F3 near by the rotation position F2 in addition to the rotation position F2, which is the target rotation position, by watching the display region R. Specifically, the C-arm 9 rotates from the rotation position F1 to the rotation position due to running of the rotation instruction switch 45 (Step S5). Once the C-arm 9 reaches to the rotation position F2, the additional information TA referring to FIG. 12 is changed to the additional information TB (Step S6). The operator confirms the additional information TB and then operates the irradiation instruction switch 47 to irradiate the X-ray (Step S7). The X-ray irradiation action triggers the target position identification element 51 to change the target rotation position from the rotation position F2 to the rotation position F3 (Step S8).

Since then, the steps from Step S3 to Step S8 are repeated in series corresponding to the number of the rotation positions. Once the action for the X-ray irradiation relative to Step S7 is performed at the rotation position F9 which is the latest rotation position of the C-arm 9, the sequence mode is ended by operating the end switch not shown in FIG.

According to the present Embodiment, even when the sequence information SQ1 includes nine rotation position information, all rotation position information are not displayed on the touch panel 43. Specifically, the number of the rotation positions that can be displayed simultaneously displayed on the touch panel 43 is limited to the predetermined number in advance (four in the present Embodiment) by the read-out element 53. Specifically, for example, only the present target rotation position, the next target rotation position and the latest target rotation position, which are of the limited number of the information including the information of the important rotation position for proceeding the sequence mode, can be displayed on the touch panel 43. Therefore, the visual recognition level of the displayed information can be improved, so that such as an important information, e.g., the present target rotation position information, can be easily and quickly confirmed.

In addition, the maximum number of the rotation position information read out by the read-out element 53 in Step S3 is four, but the read-out number varies depending on the proceeding state of the sequence mode. Provided the target rotation position is the rotation position F1, no display object exists in the display region R4, so that the number of information that the read-out element 53 read out is three. Provided the target rotation position is the rotation position F2 or F7, the information of all display regions R1-R4 is displayed, so that the number of information that the read-out element 53 read out is three.

Figure 13:
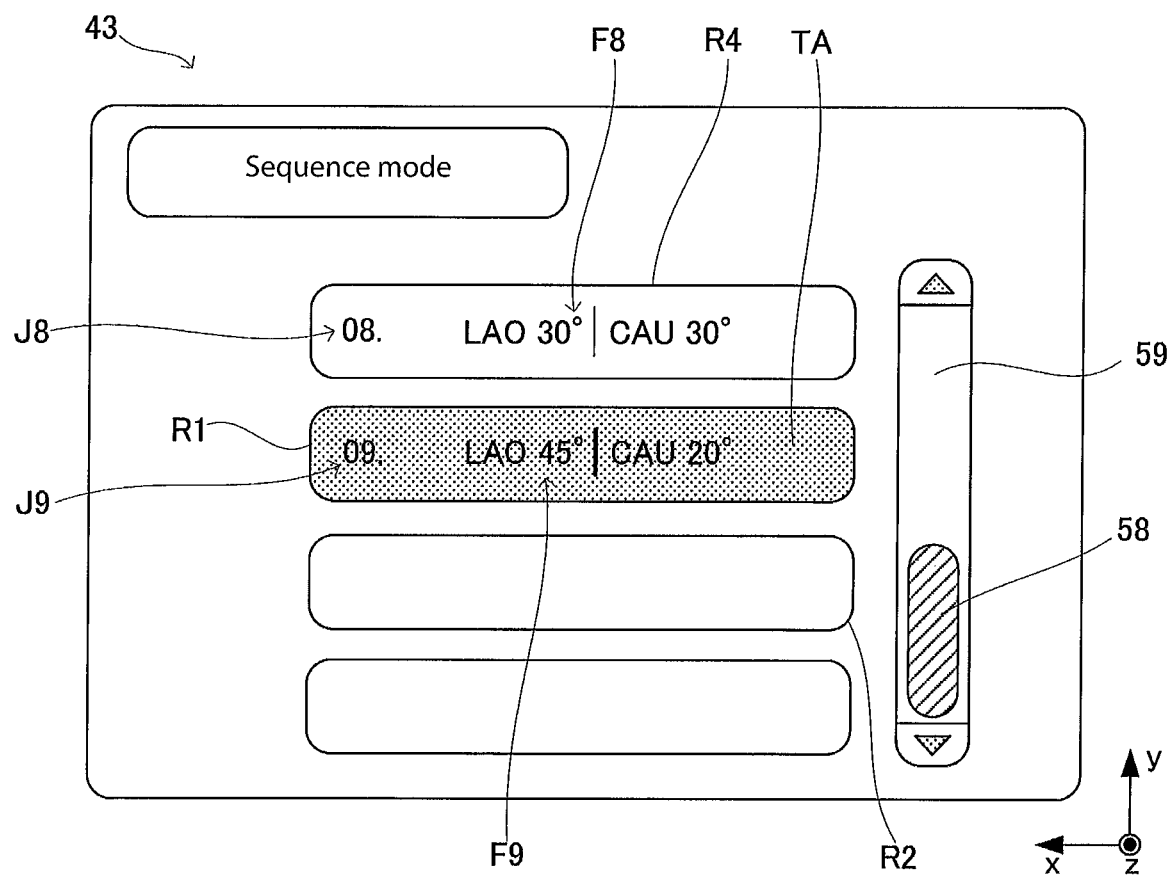
FIG. 13 is the view illustrating the touch panel display screen at the Step S4 when the target rotation position at the present time is the rotation position F9 according to the Embodiment.

Provided the target rotation position is the rotation position F8, no information of the object to be displayed in the display region R3 exists, so that the number of information that the read-out element 53 reads out is three. Provided the target position of the rotation position is the rotation position F9, no information of the next target rotation position exists, so that no information of the object to be displayed in the display region R2 and the display region R3 exists. Accordingly, the number of information that the read-out element 53 reads out is two. As a result, the display screen in the touch panel 43 is as shown in FIG. 13. Specifically, the information of the rotation position F9 that is the target rotation position at the present time is displayed in the display region R1, and the information of the rotation position F8 that is the latest target rotation position is displayed in the display region R4.

Effects of the Aspect of the Embodiment

Term 1

An X-ray fluoroscopic imaging apparatus, according to the present Embodiment, comprises: an X-ray tube 5 that irradiates an X-ray to a subject M; an X-ray detector 7 that detects the X-ray is in place facing the X-ray tube 5, detects the X-ray transmitting the subject M; a C-arm 9 that supports the X-ray tube 5 and the X-ray detector 7 while facing each other and is rotatable around the respective two axes that are orthogonal to each other; a rotation position detection element 33 that detects the information related to the position of the C-arm 9 as a position information; a memory storage element 37 that stores a plurality of position information, as the sequence information SQ1, so as to correspond to the order information for the C-arm 9 that rotates to such a position; a touch panel 43 that displays the position information included in the sequence information SQ1 in parallel along the order of rotations of the C-arm 9; and a display control element 55 that controls the touch panel 43 to display the position information corresponding to the target rotation position in the predetermined fixed region R1 of the touch panel 43, which is the position of the C-arm 9 that irradiates next the X-ray among the position information included in the sequence information SQ1, every time when the X-ray tube 5 irradiates the X-ray.

Figure 14:
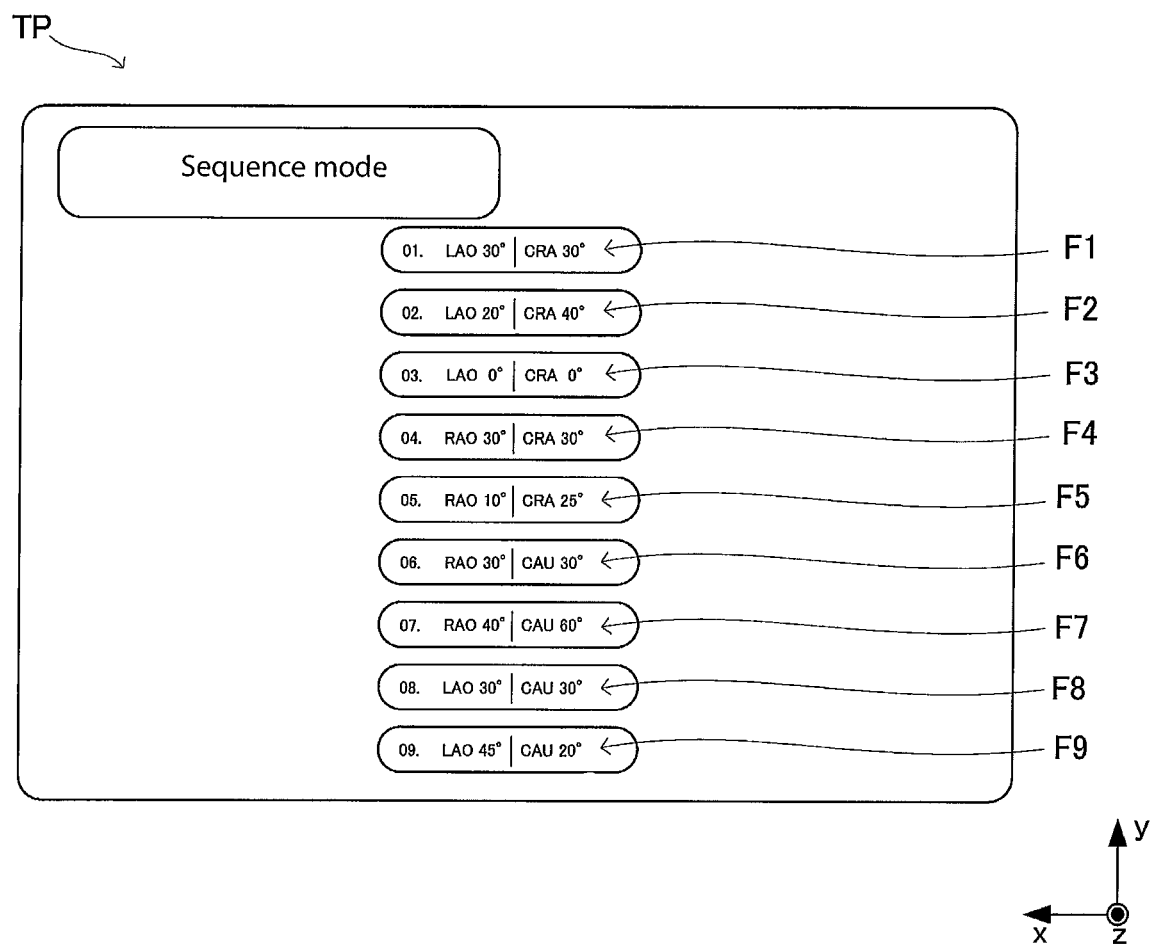
FIG. 14 is a view illustrating a touch panel display screen according to the conventional Embodiment
Figure 16:
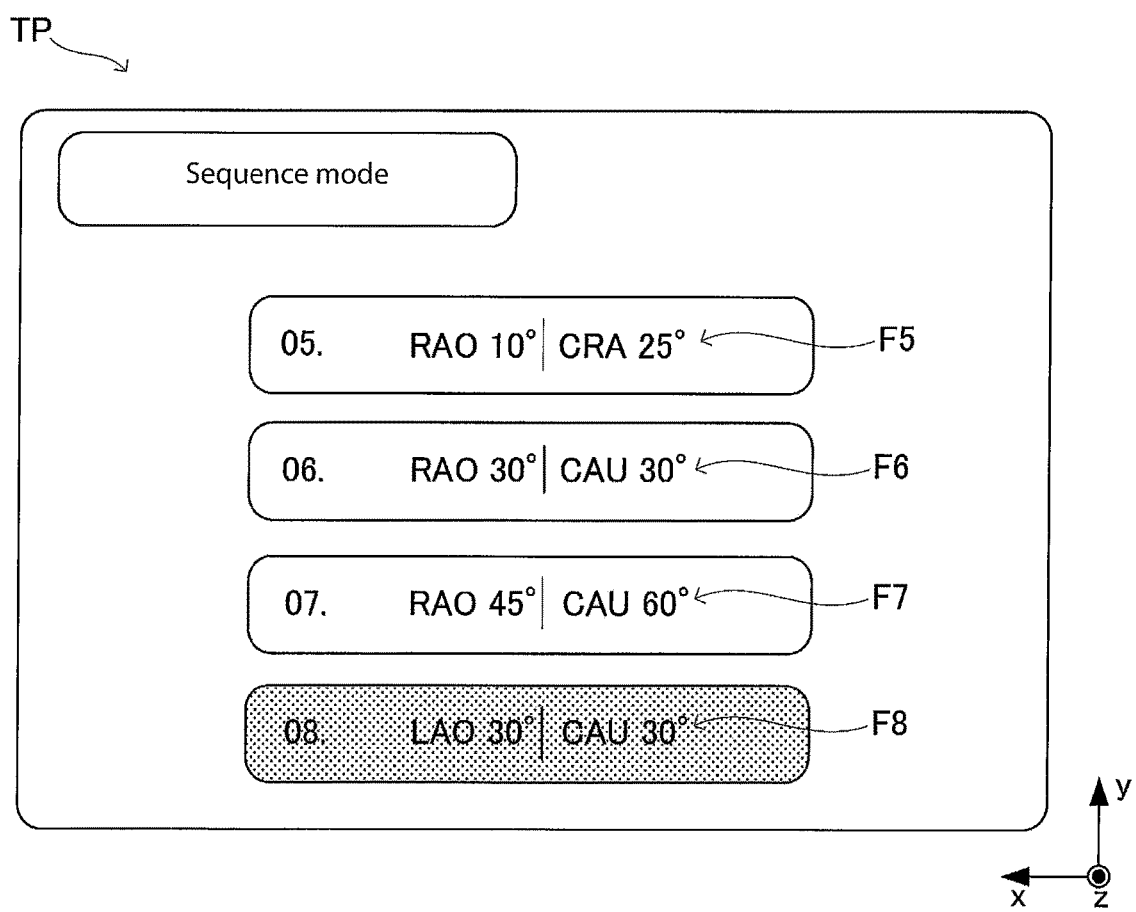
FIG. 16 is the view illustrating the touch panel display screen when the target rotation position at the present time is the rotation position F8 according to the comparative Embodiment.

The inventors set forth an effect due to the fluoroscopic imaging apparatus 1 described in Term 1 referring to FIG. 14 or FIG. 16. FIG. 14 is a view illustrating a display screen of the touch panel TP used in a conventional X-ray fluoroscopic imaging apparatus 1. In addition, the content of the sequence information used in such a conventional apparatus is the same as the sequence information SQ1 referring to FIG. 4.

According to the conventional apparatus, all information of the rotation positions F1-F9 included in the sequence information SQ1 referring to FIG. 14 is simultaneously displayed in the touch panel 43. In such a structure, the information volume displayed in the touch panel 43 proportionally increases the number of the rotation positions included in the sequence information SQ1. Therefore, when the operation operates for the C-arm to travel a number of rotation positions using the sequence mode, the operator must find out the target rotation position from a vast number of the target rotation positions that are displayed in the touch panel 43. As a result, the operator is required to move and cast the eye at the entire area of the touch panel 43 for a long time without stopping to understand the information of the target rotation position, which is particularly the important information relative to the rotation positions, so that the workload thereon increases, and the operation takes a longer period of time.

Figure 15:
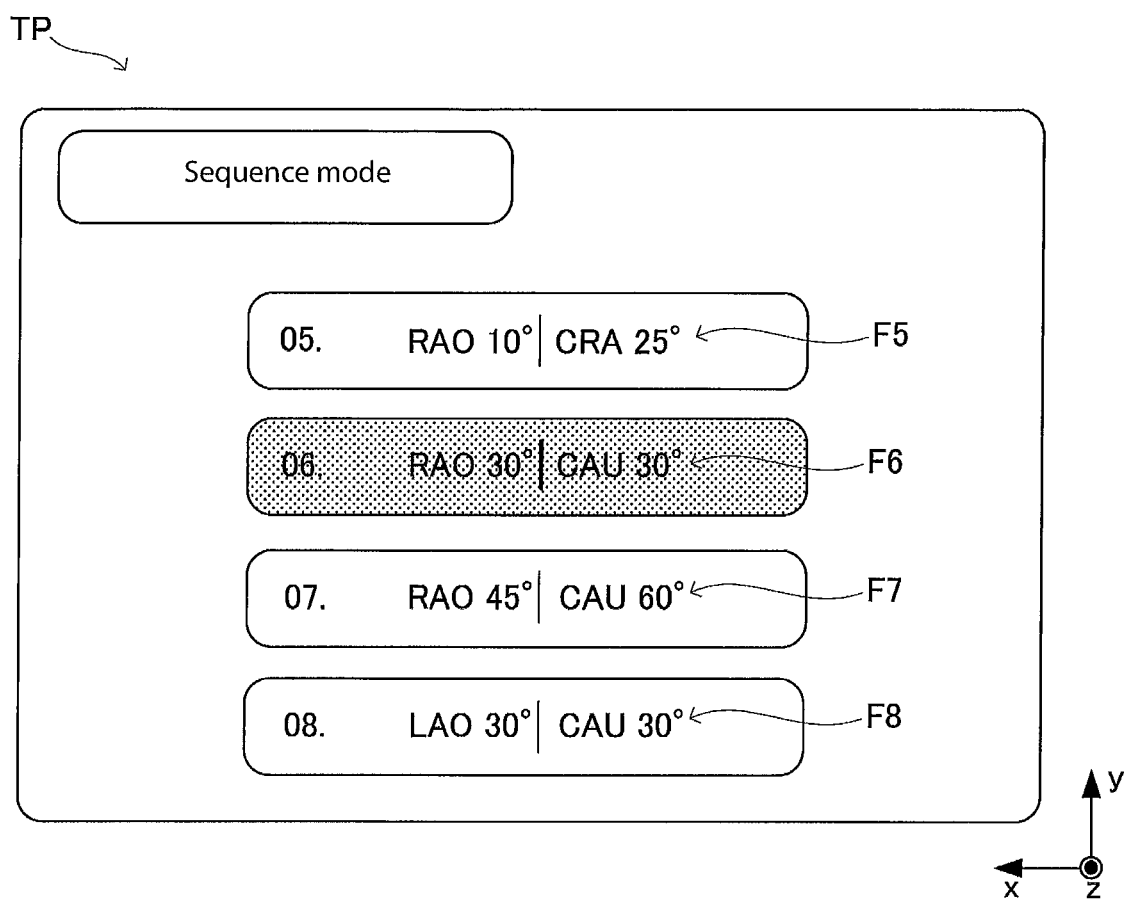
FIG. 15 is the view illustrating the touch panel display screen when the target rotation position at the present time is the rotation position F6 according to the comparative Embodiment.

As a conventional comparison Embodiment to improve a visual recognition of the touch panel TP, it may be proposed that not only the target rotation position is displayed in a different manner from the other target position but also, at the same time, the number of the rotation positions being displayed in the touch panel TP are limited less than the predetermined value. FIG. 15 is a view illustrating a touch panel TP relative to the conventional comparison Embodiment. The touch panel TP according to the comparison Embodiment not only limits the number of the rotation positions displayed in the touch panel TP at the same time to not more than 4 (four) but also displays the rotation position corresponding to the target rotation position in a different color. Referring to FIG. 15, the rotation positions F5-F8 are displayed in the touch panel TP and the rotation position F6 denotes the target rotation position.

Whereas, even in such a comparison Embodiment, it is difficult to improve sufficiently the visual recognition in the touch panel relative to the sequence mode. Specifically, the respective rotation positions displayed in the touch panel TP are not changed on the screen of the touch panel TP. Accordingly, once the target rotation position is changed following the action that proceeds due to the sequence mode, the position of the region displayed in the different manner is being changed together with the target rotation position.

FIG. 16 is illustrating the touch panel TP according to the comparison Embodiment, in which the target rotation position is the rotation position F8. Specifically, the displayed portions of the rotation positions F5-F8 are fixed, so that the center region of the touch panel TP, at which the rotation position F6 is fixed and displayed, is emphasized with a different color (as a halftone here) referring to FIG. 15 when the target rotation position is the rotation position F6.

Whereas, the lower bottom region of the touch panel TP, at which the rotation position F8 is fixed and displayed, is emphasized with the different color referring to FIG. 16 when the target rotation position is changed to the rotation position F8 following the proceeding of the operation due to the sequence mode. In such a way, when the sequence mode proceeds, the region emphasized as the target rotation position changes, so that the operator must look for the emphasized and displayed region as the target rotation position by moving the sight all over the area of the touch panel TP every time when the operator casts an eye again at the touch panel TP following looking away from the touch panel TP. As a result, it takes a longer time to confirm the target rotation position at the present time and the operator's workload increases.

The X-ray fluoroscopic imaging apparatus 1 according to the present Embodiment displays the information of the target rotation position of the C-arm 9 at the present time from the rotation positions F1-F9 included in the sequence information SQ1 in the predetermined prefixed region of the touch panel 43. In other words, even when the rotation position corresponding to the target rotation position at the present time changes according to the proceeding of the sequence mode, the newly changed target rotation position is newly displayed in such a fixed region.

Therefore, even when looking away once from the touch panel 43, the operator can confirm absolutely the target rotation position at the present time by casting the eye at such a fixed region in the touch panel 43. Specifically, it is not required to look all over the touch panel 43 to look for the target rotation position while moving line of sight when confirming the position information of the target rotation position. Accordingly, the operator confirms quickly and without tiredness the position information of the target rotation position at the present time, which is the most important information among the rotation position information with regard to the sequence mode.

Term 2

In addition, with regard to the fluoroscopic imaging apparatus according to the term 1, the predetermined fixed region, in which the target rotation position is displayed in the touch panel 43, is the center region of the touch panel 43.

In such a structure, even when the target rotation position at the present time changes due to the proceeding of the sequence mode, the information of the position identified as the target rotation position at the present time is displayed in the center of the touch panel 43. The center region of the touch panel 43 provides particularity a high visual recognition level and the information in such a region can be easily caught up by eyes. Therefore, if the touch panel 43 is controlled so that the information of the target rotation position at the present time is being constantly displayed in the center region thereof, the operator can confirm further easily and quickly the information of the target rotation position at the present time.

Term 3

In addition, with regard to the fluoroscopic imaging apparatus according to the term 1 or term 2, the display control element 55 controls the touch panel 43 so that the position information corresponding to the next rotation position of the C-arm 9 to such target rotation position is displayed adjacent to the position information corresponding to the target rotation position of the C-arm 9, which is displayed in the fixed region of the touch panel 43.

With regard to the X-ray fluoroscopic imaging apparatus according to the term 3, the target rotation position at the present time is constantly displayed in the fixed region of the touch panel 43, and also the position information of the rotation position of the next target rotation position is constantly displayed in the region adjacent to the information of the target rotation position. In such a structure, the operator can understand absolutely and easily both the target rotation position at the present time and the rotation position of the next target rotation position by just slightly moving the line of sight from such a fixed region to the adjacent region following casting the eye at the fixed region.

The inventors studied extensively and as a result realizes that it is very important to catch up constantly not only the target rotation position at the present time but also the information of the rotation position of the next target rotation position among a plurality of information of the rotation positions included in the sequence information, when executing the operation due to the sequence mode. In addition, it is now understood that it is difficult and problematic to catch up constantly the information of the rotation position, which is the next target rotation position, using the conventional apparatus.

The inventors set forth problems to be solved relative to the conventional apparatus referring to FIG. 15 and FIG. 16. Conventionally, when the rotation position included in the sequence information is displayed, the display positions of the respective rotation positions are fixed. Accordingly, when the target rotation position changes following the operation proceeding due to the sequence mode, the display position of the target rotation position, which is the important information, changes the position right after the other position on the touch panel TP screen. Specifically, following the operation proceeding, the state in which the target rotation position is displayed in the center region of the touch panel TP (FIG. 15) changes to the state in which the target rotation position is displayed in the lower bottom region of the touch panel TP (FIG. 16).

Referring to FIG. 16, target rotation position at the present time is F8, so that the rotation position of the next target rotation position is F9. Whereas, referring to FIG. 16, the rotation position information being displayed in the touch panel TP is the rotation position F5-F8, so that the operator cannot confirm the position information relative to the next target rotation position even if casting the eye at the touch panel TP. Therefore, it is difficult to intuitively understand the pathway, on which the C-arm rotates from the target rotation position at the present time to the next target rotation position, and the arriving timing at the next target rotation position. In such a way, according to the conventional structure in which the display region of the target rotation position at the present time changes, the incident, in which the information of the next target rotation position cannot be confirmed, may take place, so that it is difficult to proceed adequately the examination or the operation while predicting the rotation position of the C-arm and the timing thereof.

Whereas, with regard to the X-ray fluoroscopic imaging apparatus 1 according to the present Embodiment, not only the target rotation position at the present time is constantly displayed in the fixed region of the touch panel 43, but also the position information of the rotation position of the next target rotation position is constantly displayed in the region adjacent to the target rotation position. Specifically, while the target rotation position changes sequentially due to the proceeding of the sequence mode, the information of the target rotation position at the present time and the information of the next target rotation position are constantly displayed on the touch panel 43. Therefore, the operator can understand absolutely the information of the respective two positions information casting an eye at the touch panel 43. Consequently, the examination and the procedural operation can be progressed adequately while predicting the rotation position and the timing of the C-arm.

In addition, the position information of the next target rotation position is constantly displayed to be adjacent to the target rotation position at the present time. Therefore, the operator can confirm the target rotation position at the present time and the next target rotation position by just slightly moving the line of sight from such a fixed region in which the target rotation position at the present time is displayed. Accordingly, the operator can be escaped from a fatigue when understanding such two positions information.

Term 4

In addition, with regard to the fluoroscopic imaging apparatus according to the term 1 or term 3, the display control element 55 controls the touch panel 43 so that the position information corresponding to the rotation position of the C-arm 9 right before the target rotation position at the present time, the position information corresponding to the target rotation position of the C-arm 9 at the present time and the position information corresponding to the next target rotation position of the C-arm 9 at the present time are displayed in series to be adjacent to one another.

With regard to the X-ray fluoroscopic imaging apparatus according to the term 4, not only the target rotation position at the present time is constantly displayed in the fixed region of the touch panel 43, but also the position information corresponding to the rotation position of the C-arm 9 right before such a target rotation position are constantly displayed in the region adjacent to the information of the target rotation position. In such a structure, the operator can understand absolutely and easily both the target rotation position at the present time and the rotation position of the next target rotation position by just slightly moving the line of sight from such a fixed region to the adjacent region following casting the eye at the fixed region.

The inventors now realize that it is very important to constantly catch up the information of the rotation position right before it was the target rotation position as well as the information of the position of the target rotation position at the present time among a plurality of information of the rotation positions included in the sequence information. And it is now also understood that it is difficult and problematic to constantly catch up the information of the rotation position that was the target rotation position right before using the conventional apparatus.

With regard to the conventional structure, referring to FIG. 15 or FIG. 16, given the target rotation position at the present time is the rotation position F5 when the rotation positions F5-F8 are displayed in the touch panel TP, the rotation position that is the target rotation position right before corresponds to the rotation position F4. Regardless, the rotation position F4 and the rotation position F5 are not simultaneously displayed in the touch panel TP, so that the operator hardly understands the pathway from the rotation position F4 to the rotation position F5. In such a way, when the rotation position F5 being displayed in the upper end is the target rotation position, the information of the rotation position F4 that is the target rotation position right before cannot be confirmed on the touch panel TP.

The target rotation position is the rotation position to be the target position for the C-arm to rotate for the next X-ray irradiation. Specifically, the latest target rotation position corresponds to the present position of the C-arm in between the time right after X-ray irradiation and the time to start rotation of the C-arm. Therefore, the information of the latest target rotation position is highly important in association with understanding the pathway in advance, in which the C-arm travels due to such a rotation operation, at the time when the C-arm starts to rotate.

With regard to the fluoroscopic imaging apparatus 1 according to the present Embodiment, the touch panel 43 is controlled so that the position information of the position that is the latest target rotation position, the information of the target rotation position at the present time and the position information of the next target rotation position are displayed in series to be adjacent to one another. In such a structure, even if the rotation position identified as the target rotation position changes due to the proceeding of the sequence mode, the position information of the latest target rotation position, the position information of the target rotation position at the present time and the position information of the next target rotation position are constantly displayed on the touch panel 43. Therefore, the operator can understand absolutely the three positions information by casting an eye at the touch panel 43. Consequently, the examination and the procedural operation action can be performed adequately while predicting the rotation pathway of the C-arm 9 and the rotation timing thereof.

In addition, the information of the latest target rotation position and the information of the next target rotation position are displayed to be constantly adjacent to the information of the target rotation position at the present time. Therefore, the operator can confirm the target rotation position at the present time, the next target rotation position and the latest target rotation position by just slightly moving the line of sight from the fixed region in which the target rotation position at the present time is displayed. Accordingly, the operator can be escaped from a fatigue when understanding such three positions information.

Term 5

The X-ray fluoroscopic imaging apparatus according to any one of the term 1 or the term 4 comprises the read-out element 53 that selects the predetermined number of the position information including the position information corresponding to the target rotation position of the C-arm 9 at the present time from information of a plurality of rotation positions F1-F9 included in the sequence information SQ1, and the display control element 55 controls the touch panel 43 to display the information of the predetermined rotation positions selected by the read-out element 53.

With regard to the X-ray fluoroscopic imaging apparatus according to the term 5, the read-out element 53 and the display control element 55 selectively display the predetermined number of the rotation positions including the target position information at the present time from the position information of a plurality of rotation positions F1-F9 included in the sequence information SQ1 in touch panel 43. Specifically, even when the sequence information includes a number of position information SQ1, the number of the position information to be displayed on the touch panel 43 can be limited not more than the predetermined the number. Accordingly, a visibility (visual recognition level) of the position information displayed on the touch panel 43, particularly, the visibility of the information relative to the target rotation position at the present time can be improved.

OTHER EMBODIMENTS

Specifically, the aspects of the Embodiment disclosed at this time are examples and not limited thereto in any points. The scope of the present invention is specified in the claims and all alternatives are included in the scope of the claims and equivalents thereof. For example, the present invention can be implemented in the below alternative Embodiment.

(1)

According to the present Embodiment set forth above, for example, the touch panel 43 has four display region R1-R4, but the number of the display regions is not limited thereto. An Embodiment may have two fixed display regions R1 and R2, the target rotation position at the present time may be constantly displayed in the display region R1 and the position information of the next target rotation position may be constantly displayed in the display region R2.

(2)

According to the Embodiment and the alternative Embodiment set forth above, the rotation position information of the latest target rotation position, the information of the target rotation position at the present time and the rotation position information of the next target rotation position are simultaneously displayed on the touch panel 43, but these three kinds of information are not limited to be simultaneously displayed. Specifically, two of the rotation position information of the latest target rotation position and the information of the target rotation position at the present time may be simultaneously displayed in the touch panel 43. Further, two of the information of the target rotation position at the present time and the rotation position information of the next target rotation position may be simultaneously displayed on the touch panel 43.

(3)

According to the Embodiment and the alternative Embodiment set forth above, the display region R1 that displays the information of the target rotation position at the present time is constantly displayed in the center of the touch panel 43, but the Embodiment is not limited thereto. Specifically, as long as the information of the target rotation position at the present time is constantly displayed in the predetermined fixed region, the fixed region in which the display region R1 is in place on the touch panel 43 may be set to be the arbitrary position on the touch panel 43.

(4)

According to the Embodiment and the alternative Embodiment set forth above, the Embodiment with regard to the position information comprising the rotation angle in the body axis direction of the subject M as the position information of the C-arm 9 and the rotation angle around the circumference of the body axis of the subject M are set forth, but not limited thereto. For example, the information of the turning angle around the perpendicular axis RC obtained by the rotary encoder R3 may be assigned to the position information of the C-arm 9. Further, the combined information of the rotation angle in the body axis direction obtained by the rotary encoder R1, the rotation angle around circumference of the body axis obtained by the rotary encoder R2 and the information of the turning angle obtained by the rotary encoder R3 may be assigned to the position information of the C-arm 9.

REFERENCE OF SIGNS

1 X-ray fluoroscopic imaging apparatus
3 Table
5 X-ray tube
7 X-ray detector
9 C-arm (support mechanism)
17 Collimator
29 X-ray irradiation control element
30 Image generation element
31 Image display element
33 Rotation position detection element
35 Main control element
37 Memory element
39 Console
41 Arm operation lever
43 Touch panel
45 Rotation instruction switch
47 Imaging instruction switch
51 Target position identification element
53 Read-out element
55 Display control element
57 Information addition element It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray Fluoroscopic imaging and X-Ray related diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible, and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and images and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets, hand-held devices and other platform tablets, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopic imaging apparatus, comprising:
an X-ray tube that irradiates an X-ray toward a subject;
an X-ray detector is in place facing said X-ray tube and detects said X-ray transmitting said subject;
a support mechanism supports said X-ray tube and said X-ray detector to face each other and is rotatable around two respective axes that are orthogonal to each other;
a rotation position detection element that detects an information related to a position of said support mechanism as a position information;
a memory storage element that stores a plurality of positions information as a sequence information in association with information of a rotation order in which said support mechanism rotates to an appropriate position;
a position information display element that displays said position information included in said sequence information in parallel and in order of rotations of said support mechanism;
a display control element that controls said position information display element to display said position information in a predetermined fixed region of said position information display element every time when said X-ray tube irradiates said X-ray; and
wherein said position information is one of said positions information included in said sequence information and corresponds to a target position that is a position of said support mechanism that irradiates next said X-ray.

2. The X-ray imaging apparatus according to claim 1, wherein:
said fixed region is a center region of said position information display element.

3. The X-ray imaging apparatus according to claim 1, wherein:
said display control element controls said position information display element to display said position information corresponding to a position to which said support mechanism rotates to irradiate said X-ray following said target position at a present time adjacent to said position information corresponding to said target position displayed in said fixed region.

4. The X-ray imaging apparatus according to claim 1, wherein:
said display control element controls said position information display element to display said position information corresponding to said position at which said X-ray is irradiated next following rotation of said latest target position of said support mechanism; and
wherein said position information corresponding to said target position of said support mechanism at said present time and said position information corresponding to said position at which said X-ray is irradiated next following said rotation of said support mechanism to said target position at said present time are adjacently displayed respectively in series.

5. The X-ray imaging apparatus according to claim 1, further comprising:
a position information selection element that selects a predetermined number of said position information including said position information corresponding to said target position of said support mechanism at said present time from among a plurality of said positions information included in said sequence information, and
wherein said display control element controls for displaying said predetermined number of said positions information that said position information selection element selects.

* * * * *